US009974839B2

(12) United States Patent
Nitsche et al.

(10) Patent No.: US 9,974,839 B2
(45) Date of Patent: May 22, 2018

(54) SELF-ASSEMBLED TOROIDAL-SPIRAL PARTICLES AND MANUFACTURE AND USES THEREOF

(71) Applicant: THE BOARD OF TRUSTEES OF THE UNIVERSITY OF ILLINOIS, Urbana, IL (US)

(72) Inventors: Ludwig C. Nitsche, Chicago, IL (US); Ying Liu, Clarendon Hills, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 453 days.

(21) Appl. No.: 14/456,736

(22) Filed: Aug. 11, 2014

(65) Prior Publication Data

US 2015/0030686 A1 Jan. 29, 2015

Related U.S. Application Data

(62) Division of application No. 13/510,214, filed as application No. PCT/US2010/056937 on Nov. 17, 2010, now Pat. No. 8,852,645.

(60) Provisional application No. 61/281,576, filed on Nov. 19, 2009.

(51) Int. Cl.

| | |
|---|---|
| ***A61K 38/38*** | (2006.01) |
| ***A61K 31/337*** | (2006.01) |
| ***A61K 31/351*** | (2006.01) |
| ***A61K 9/14*** | (2006.01) |
| ***A61K 9/16*** | (2006.01) |
| ***A61K 38/18*** | (2006.01) |

(52) U.S. Cl.
CPC ............ *A61K 38/385* (2013.01); *A61K 9/146* (2013.01); *A61K 9/1641* (2013.01); *A61K 31/337* (2013.01); *A61K 31/351* (2013.01); *A61K 38/1866* (2013.01)

(58) Field of Classification Search
None
See application file for complete search history.

(56) References Cited

U.S. PATENT DOCUMENTS

| | | | |
|---|---|---|---|
| 2005/0084534 | A1 | 4/2005 | Ni et al. |
| 2008/0317666 | A1 | 12/2008 | Fattal et al. |
| 2010/0152880 | A1 | 6/2010 | Boyden et al. |

FOREIGN PATENT DOCUMENTS

WO WO-2008/061963 A2 5/2008

OTHER PUBLICATIONS

Afuwape, A., et al., "The Role of the Angiogenic Molecule VEGF in the Pathogenesis of Rheumatoid Arthritis," *Histology and Histopathology*, 2002, vol. 17, pp. 961-972.

Blandino, A., et al., "Formation of Calcium Alginate Gel Capsules: Influence of Sodium Alginate and $CaCl_2$ Concentration on Gelation Kinetics," *Journal of Bioscience and Bioengineering*, 1999, vol. 88, No. 6, pp. 686-689.

(Continued)

*Primary Examiner* — Bethany P Barham
*Assistant Examiner* — Barbara S Frazier
(74) *Attorney, Agent, or Firm* — Marshall, Gerstein & Borun LLP

(57) ABSTRACT

Toroidal-spiral shaped particles, their method of manufacture, and uses thereof are disclosed. The toroidal-spiral particles can contain at least one active agent, such as a drug, and provide a controlled, sustained release of the active agent.

12 Claims, 7 Drawing Sheets

(56) References Cited

OTHER PUBLICATIONS

Chen, D., et al., "The Chemistrode: A Droplet-Based Microfluidic Device for Stimulation and Recording With High Temporal, Spatial, and Chemical Resolution," *Proceedings of the National Academy of Sciences of the United States of America*, 2008, vol. 105, No. 44, pp. 16843-16848.

Chung, H., et al., "Heparin Immobilized Porous PLGA Microspheres for Angiogenic Growth Factor Delivery," *Pharmaceutical Research*, 2006, vol. 23, No. 8, pp. 1835-1841.

Desai, N., et al., "Biological Responses to Polyethylene Oxide Modified Polyethylene Terephthalate Surfaces," *Journal of Biomedical Materials Research*, 1991, vol. 25, pp. 829-843.

Dill, K., "Dominant Forces in Protein Folding," *Biochemistry*, 1990, vol. 29, No. 31, pp. 7133-7155.

Dobson, C., "Experimental Investigation of Protein Folding and Misfolding," *Methods*, 2004, vol. 34, pp. 4-14.

Dobson, C., "Principles of Protein Folding, Misfolding and Aggregation," Seminars in *Cell & Developmental Biology*, 2004, vol. 15, pp. 3-16.

Dobson, C., "Protein Folding and Misfolding," *Nature*, 2003, vol. 426, pp. 884-890.

Fedakar-Senyucel, Mine, et al., The Effects of Local and Sustained Release of Fibroblast Growth Factor on Wound Healing in Esophageal Anastomoses, *Journal of Pediatric Surgery*, 2008, vol. 43, pp. 290-295.

Ghandi, M., et al., "Mechanistic Examination of Protein Release from Polymer Nanofibers," *Molecular Pharmaceutics*, 2009, vol. 6, No. 2, pp. 641-647.

Hill-West, J., etal., "Inhibition of Thrombosis and Intimal Thickening by in Situ Photopolymerization of thin Hydrogel Barriers," *Proceedings of the National Academy of Sciences of the United States of America*, 1994, vol. 91, pp. 5967-5971.

Hoare, T., et al., "Hydrogels in Drug Delivery: Progress and Challenges," *Polymer*, 2008, vol. 49, pp. 1993-2007.

Itoh, Y., et al., "Locally Controlled Release of Basic Fibroblast Growth Factor from Multilayered Capsules," *Biomacromolecules*, 2008, vol. 9, pp. 2202-2206.

Kolterman, O., et al., "Pharmacokinetics, Pharmacodynamics, and Safety of Exenatide in Patients with Type 2 Diabetes Mellitus," *American Journal of Health-System Pharmacy*, 2005, vol. 62, No. 2, pp. 173-181.

Koutsopoulosa, S., et al., "Controlled Release of Functional Proteins Through Designer Self-Assembling Peptide Nanofiber Hydrogel Scaffold," *Proceedings of the National Academy of Sciences of the United States of America*, 2009, vol. 106, No. 12, pp. 4623-4628.

Krishnamurthy, R., et al., "The Stability Factor: Importance in Formulation Development," *Current Pharmaceutical Biotechnology*, 2002, vol. 3, pp. 361-371.

Laham, R., et al., "Local Perivascular Delivery of Basic Fibroblast Growth Factor in Patients Undergoing Coronary Bypass Surgery," *Circulation*, 1999, vol. 100, pp. 1865-1871.

Lee, H., et al., "Preparation and Characterization of Mono-PEGylated Epidermal Growth Factor: Evaluation of in Vitro Biologic Activity," *Pharmaceutical Research*, 2002, vol. 19, No. 6, pp. 845-851.

Lewis, B., et al., "Angiogenesis by Gene Therapy: a New Horizon for Myocardial Revascularization?" *Cardiovascular Research*, 1977, vol. 35, pp. 490-497.

Machu, G., et al., "Coalescence, Torus Formation and Breakup of Sedimenting Drops: Experiments and Computer Simulations," *Journal of Fluid Mechanics*, 2001, vol. 447, pp. 299-336.

Markussen, J., et al., "Soluble, Fatty Acid Acylated Insulins Bind to Albumin and Show Protracted Action in Pigs," *Diabetologia*, 1996, vol. 39, pp. 281-288.

Mellott, M., et al., "Release of Protein From Highly Cross-Linked Hydrogels of Poly(ethylene glycol) Diacrylate fabricated by UV polymerization," *Biomaterials*, 2001. vol. 22, pp. 929-941.

Murata, Y., et al., "Influence of Erosion of Calcium-Induced Alginate Gel Matrix on the Release of Brilliant Blue," *Journal of Controlled Release*, 1993, vol. 23, pp. 21-26.

Nitsche, L., et al., "Wavelets and Fast Summations for Particle Simulations of Gravitational Flows of Miscible Drops," *Computers and Chemical Engineering*, 2004, vol. 28, pp. 1873-1879.

Post, M., et al., "Therapeutic Angiogenesis in Cardiology Using Protein Formulations," *Cardiovascular Research*, 2001, vol. 49, pp. 522-531.

Putney, S., et al., "Improving Protein Therapeutics With Sustained-Released Formulations," *Nature Biotechnology*, 1998, vol. 16, No. 2, pp. 153-157.

Sawhney, A., et al., Optimization of Photopolymerized Bioerodible Hydrogel Properties for Adhesion Prevention, *Journal of Biomedical Materials Research*, 1994, vol. 28, pp. 831-838.

Schulze, S., et al., "Lipid Extrudates as Novel Sustained Release Systems for Pharmaceutical Proteins, "*Journal of Controlled Release*, 2009, vol. 134, pp. 177-185.

Segers, V., et al., "Local Delivery of Proteins and the Use of Self-Assembling Peptides," *Drug Discovery Today*, 2007, vol. 12, Nos. 13/14, pp. 561-568.

Stefani, M., et al., "Protein Aggregation and Aggregate Toxicity: New Insights Into Protein Folding, Misfolding Diseases and Biological Evolution," *Journal of Molecular Medicine*, 2003, vol. 81, pp. 678-699.

Tamber, et al., "Formulation Aspects of Biodegradable Polymeric Microspheres for Antigen Delivery," *Advanced Drug Delivery Reviews*, 2005, vol. 57, pp. 357-376.

Tao, S., et al., "Microfabricated Drug Delivery Systems: From Particles to Pores" *Advanced Drug Delivery Reviews*, 2003, vol. 55, pp. 315-328.

Veronese, F., et al., "Introduction and Overview of Peptide and Protein Pegylation," *Advanced Drug Deliver Reviews*, 2002, vol. 54, pp. 453-456.

Wissink, M., et al., "Improved Endothelialization of Vascular Grafts by Local Release of Growth Factor from Heparinized Collagen Matrices," *Journal of Controlled Release*, 2000, vol. 64, pp. 103-114.

Ylä-Herttuala, S., et al., "Cardiovascular Gene Therapy," *The Lancet*, 2000, vol. 355, pp. 213-222.

International Search Report in International Application No. PCT/US2010/056937, dated Jul. 28, 2011.

FIGURE 8A
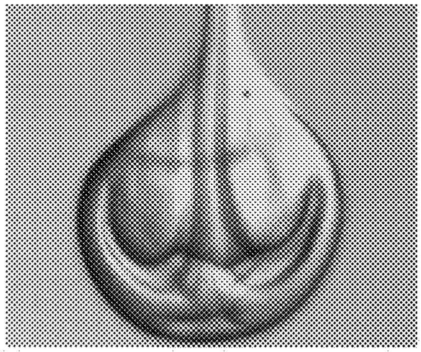
FIGURE 8B
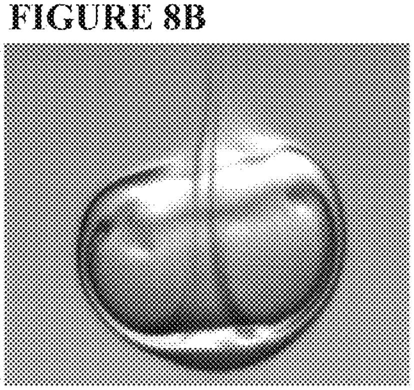
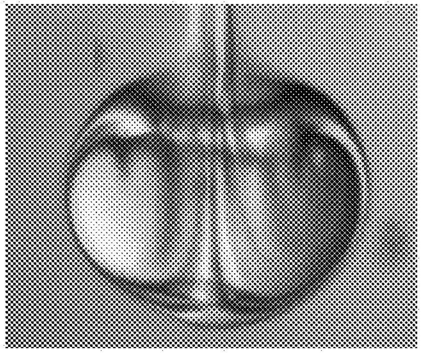
FIGURE 8C
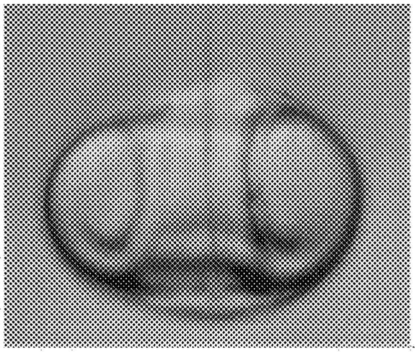
FIGURE 8D
FIGURE 8E
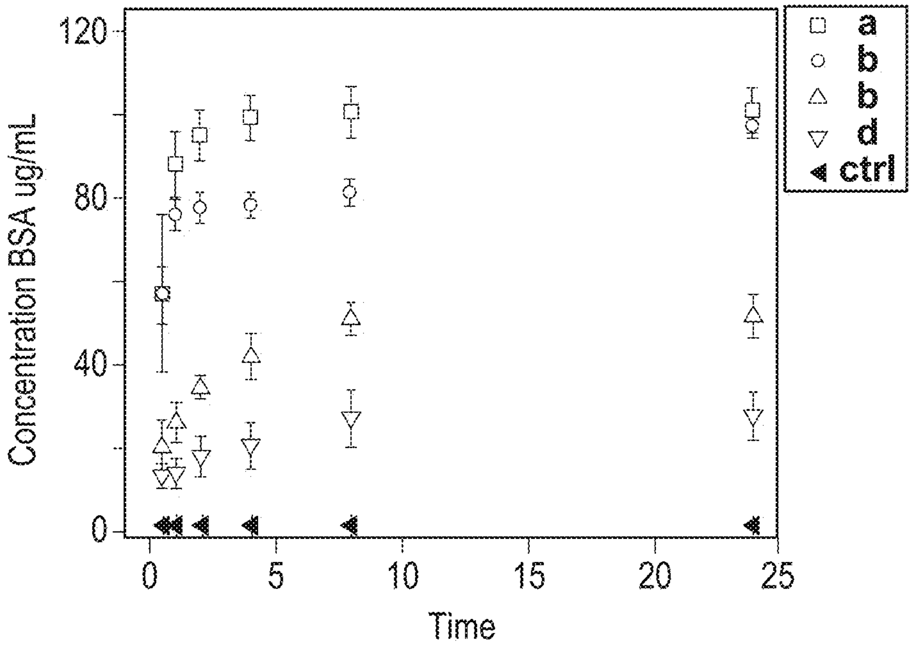

SELF-ASSEMBLED TOROIDAL-SPIRAL PARTICLES AND MANUFACTURE AND USES THEREOF

CROSS-REFERENCE TO RELATED APPLICATIONS

This is a divisional of U.S. patent application Ser. No. 13/510,214, filed Dec. 4, 2012, now U.S. Pat. No. 8,852,645, which is the U.S. national phase of International Application No. PCT/US2010/056937, filed Nov. 17, 2010, which claims the benefit of U.S. Provisional Patent Application No. 61/281,576, filed Nov. 19, 2009, incorporated herein by reference in its entirety.

FIELD OF THE INVENTION

The present invention relates to toroidal-spiral particles, their method of manufacture, and use of the particles. More particularly, the present invention relates to toroidal-spiral particles comprising one or more active agent, such as a drug or a topically-applied compound, that can provide a controlled and sustained release of the active agent.

BACKGROUND OF THE INVENTION

Proteins and peptides are vital for biological processes, and recently have attracted significant attention as therapeutic agents. Therapeutic proteins and peptides are known and used in the treatment of many serious diseases, such as diabetes, cancer, HIV, and cardiovascular diseases (3-6). In general, therapeutic proteins and peptides are considered natural, more effective, and less toxic than other drugs, such as synthetic, small molecule drugs.

However, the delivery of therapeutic proteins and peptides is challenging because bioavailability and stability must be maintained during the formulation and sustained release processes. Although there has been intense research in this area, efficacious systems for targeting delivery and sustained release of proteins and peptides in biologically active conformations and concentrations are in need.

A systemic delivery of protein therapeutic agents is feasible, e.g., exenatide for the treatment of type II diabetes (7). But high systemic levels of growth factors can cause unwanted, adverse side effects and immunogenicity, for example, carcinomas and tumor growth (8). The future of therapeutic proteins therefore lies in a focused, local delivery, as in the use of angiogenesis for the treatment of cardiovascular diseases (9).

Therapeutic proteins and peptides pose a problem that small molecule drugs do not encounter, i.e., the need to maintain bioavailability and stability during the formulation process and sustained release. Damage to proteins and peptides can occur, for example, by irreversible conformation changes, denaturation, aggregation, acid- or enzyme-catalyzed degradation, deamidation, and hydrolysis (10-15). In addition, the energy barrier for protein conformation changes in solution also is low, i.e., only 5-20 kcal/mol (16), which is comparable to water-oil interfacial tensions and hydrophobic interactions.

To prevent proteins and peptides from denaturing, an effective sustained release delivery system must meet three main requirements: (a) the formulation process should avoid exposing proteins to organic solvents, water-oil interfaces, crosslinking reagents, and large temperature fluctuations; (b) after administration to an individual, the delivery system should protect proteins and peptides from aggregation, degradation, and conformation changes prior to reaching the targeted tissues; and (c) the drug release profile and pharmacokinetic properties should be well defined and reproducible.

Despite extensive research efforts and diverse technologies developed for a targeted, sustained release of proteins and peptides, few feasible methods of delivery have emerged. Current formulation strategies include four categories: (a) forming solid microspheres or microfibers that encapsulate proteins by emulsion, double emulsion, spray dry, freeze-dry, spray freeze dry, and supercritical anti-solvent processes (17-21); (b) chemical modification, such as PEGylation (22) and acylation (23); (c) forming sustained release depots by a gelling process (24, 25); and (d) delivery by self-assembling peptides and lipids (1, 26, 27). To a certain degree, these protein delivery methods protect proteins from enzymatic degradation and provide a sustained release compared to direct injection.

Encapsulating or entrapping proteins and peptides in biocompatible and biodegradable polymeric systems is one of the most promising routes for a controlled delivery and release of these drugs. Various geometries and configurations of polymeric systems have been reported, including polymeric membranes, matrices, microspheres, and microfibers.

However, each method has its limitations. For example, polymeric membranes have a potential problem of "dose-dumping," or mass release, of entrapped material due to membrane failure. For potent therapeutic agents, dose-dumping can cause serious problems. Release of proteins also is highly dependent on the microstructure of polymer matrix, such as pore size and density. Therefore, it is difficult to reproduce the release profile for the same protein, and, for different proteins, the release system has to be redesigned.

Solid microsphere and microfiber encapsulated proteins can be delivered by injection or inhalation. The general limitations with this delivery system are (a) low loading efficiency and (b) reduced protein biological activity caused by manufacturing processes involving a high shear rate, exposing proteins to a water-oil interface, and/or high temperature fluctuations (17-21).

Hydrogels potentially are suitable carriers for the delivery of proteins and peptides. Crosslinked networks of water-soluble polymers allow slow diffusion of proteins and peptides. Despite the hydrophilicity of the polymers, the process to encapsulate proteins and peptides into hydrogel can involve UV exposure, high shear rate, exposing proteins to water-oil interfaces, or high temperature fluctuations. More importantly, the release profiles of various proteins depend on the sizes of the molecules and pore size of the hydrogels.

In general, chemical modification, such as PEGylation and acylation, reduces protein degradation and receptor-mediated uptake of the proteins from the systemic circulation (22, 23). However, large proteins have several sites that are accessible to PEGylation or acylation, which produces a high heterogeneity. For example, mono-PEGylated epidermal growth factor (EGF) with PEG 3400 at Lys28 and Lys48 was found to be significantly less active than EGF isomer PEGylated at the amino terminus in an in vitro assay for mitogenic activity (28). In addition, protein conformation and bioavailability need to be further demonstrated for the modified proteins. The disadvantage of gelling depots is that the protein or peptide may be squeezed out of the depot, which results in an initial burst release of the drug (24, 25). Delivery of proteins using lipid and self-assembling peptides has the limitations of low encapsulation rate and low system stability (1, 26, 27).

SUMMARY OF THE INVENTION

Delivery systems often are used in personal care and pharmaceutical compositions to control and/or extend release of an active agent, to protect an active agent from degradation in the composition, and/or to enable formulation of the active agent into the composition due to difficulties, such as active agent instability, solubility, or formulation esthetics.

The present invention is directed to novel toroidal-spiral particles (TSPs) for a targeted, sustained release of active agents, such as therapeutic drugs, including proteins and peptides, and topically active compounds. In contrast to present active agent delivery systems, TSPs are formed and loaded with an active agent either entirely within an aqueous phase or entirely within a non-aqueous phase, and under benign conditions (e.g., room temperature, low shear, and low interfacial tension) that maintain delicate macromolecular conformations, and thereby maximize bioactivity and bioavailability. TSPs self-assemble, and also can self-load, by viscous flow, diffusion, and a crosslinking reaction. The resulting TSPs are particularly conducive to high loadings of active agents and prolonged release profiles.

The present toroidal-spiral particle (TSP) technology therefore meets the challenge of providing a targeted, sustained drug release through an effective use of spatial and temporal concentration profiles. The present invention utilizes the self-assembly of TSPs in aqueous or nonaqueous solutions to facilitate loading, targeted delivery, and sustained release of therapeutic agents, including proteins and peptides. The present method of preparing the TSPs avoids the use of organic solvents, and all processing steps can be performed at room temperature, which maximizes protein and peptide bioavailability and stability. Compared to solid spherical particles, TSPs provide a very large surface to volume ratio, which dramatically increases drug loading efficiency and provides a well-defined and prolonged release profile.

In accordance with the present invention, TSP technology utilizes the liquid-phase toroidal-spiral shape formed during sedimentation of a droplet of polymer solution (which may exhibit Newtonian or non-Newtonian rheology) through a miscible liquid of lower density, and then solidifies the TSP shape by crosslinking the polymer. The competitive kinetics mechanism by which TSPs self-assemble and self-load is shown schematically in the scheme of FIG. 1, together with subsequent release of a loaded active agent, such as a protein or peptide.

In one embodiment of a preparation of a TSP, a polymer solution or polymer melt drips under gravity (or centrifugation) through holes in the bottom of a containing vessel. For a given hole size, a balance between gravity and interfacial tension determines a characteristic size of the droplets. The droplets are introduced into a second, miscible liquid of the same or lower density, also referred to as a "bulk solution" herein. Alternatively, drops of the polymer solution or polymer melt can be introduced below the surface of the second liquid.

The second liquid can be aqueous or non-aqueous depending upon the solubility properties of the polymer solution or melt. In accordance with an important feature of the present invention, the polymer solution or polymer melt is soluble in the second liquid. The second liquid also can contain a crosslinking agent for crosslinking the polymer to form the TSP and/or one or more active agent for loading into and onto the TSP during preparation of the TSP, i.e., self-loading. Alternately, active agents can be loaded into and onto the TSP after formation of the TSP as shown in FIG. 1, i.e., diffusion loading.

In another embodiment, a polymer solution or a molten polymer is allowed to rise through a second liquid to form the TSP. The second liquid can have a higher or lower viscosity than the polymer drop, and the second liquid has a lower density than the polymer drop. As in the above embodiment, the polymer solution or molten polymer is soluble in the second liquid.

Therefore, in general, the present invention is directed to the formation of a TSP by the downward sedimentation or buoyant rise of a drop of polymer solution or molten polymer through a second liquid of a same or different viscosity and in which the polymer solution or molten polymer is soluble. As the polymer drop passes through the second liquid, the polymer solidifies to provide a particle having a toroidal-spiral shape.

By including an active agent in the second liquid, the solidifying polymer entraps or entrains the active agent to provide a TSP loaded with the active agent. The active agent can be, for example, a medicament, like a protein, a peptide, or a small molecule drug, or a topically-active agent. The loaded TSP allows for a sustained release of the loaded active agent from the particle.

If an active agent is not present in the second liquid during the liquid-phase self-assembly process (self-loading) of a TSP, an active agent can be loaded onto previously solidified TSPs by diffusion into channels of the spiral structure after particle formation (FIG. 1). Therefore, active agent bioavailability is preserved and conformation of proteins and peptides is protected by avoiding exposure to organic solvents, temperature changes, and crosslinking agents or UV light.

The active agent-loaded TSPs can be separated from the second (bulk) liquid for formulation and therapeutic delivery purposes. Sustained release of the active agents, including proteins and peptides, in vitro or in vivo, is achieved by slow diffusion of the active agent through the spiral-shaped passages, or channels, of the TSP into the surrounding solution or tissue (FIG. 1). Active agent release profiles and patterns are related to the structure and physical properties of the TSPs, such as the number of, and width of, the channels of a TSP. Because of the well-defined channels between polymer layers in a TSP, a diffusion rate for the active agent can be designed and optimized by persons skilled in the art. Alternatively, by using pH or temperature-sensitive polymers, the TSPs can degrade or expand to release the active agent spontaneously.

The TSPs and methods of the present invention provide the following, nonlimiting features of (a) TSPs having a controlled size formed by combining gravitational sedimentation (or buoyancy), viscous flow, diffusion, and polymer crosslinking kinetics; (b) convective self-assembly process that automatically entrains and loads active agents within TSPs during TSP formation entirely in a single, aqueous or non-aqueous phase (self-loading); (c) active agent-loaded TSPs of micron dimensions, which may require greater sedimentation forces generated by centrifugation, wherein flow parameters and timescales are selected such that diffusion does not substantially modify the predominantly convective formation and loading effects observed at larger scales; (d) polymer drops that can be solidified by crosslinking using an appropriate chemical crosslinking agent or UV light, wherein, in contrast to prior microsphere crosslinking in which diffusion and reaction kinetics control the rate, crosslinking of the toroidal-spiral particles is controlled by convection and reaction kinetics because the settling polymer drops induce liquid flow and take up crosslinking agents while the structures are forming; (f) an active agent, including a protein or a peptide, loaded onto TSPs retains bioactivity and bioavailability; (g) TSPs successfully deliver active agents by diffusion over sustained time periods with predictable, reproducible release profiles; and (h) a centrifuge apparatus allows for a large-scale production of TSPs.

These and other aspects and novel features of the present invention will become apparent from the following detailed description of the preferred embodiments.

BRIEF DESCRIPTION OF THE DRAWINGS

FIG. 5A-5B shows cross-linking of toroidal-spiral drops during sedimentation. The light reflection (circled by the dashed lines) indicates that the UV light was turned on. FIG. 5A Low UV intensity. FIG. 5B Moderate UV intensity.

FIG. 8A-8E shows the release kinetics of bovine serum albumin (BSA) from diffusion-loaded TSAs and a control semi-spherical particle over time.

DETAILED DESCRIPTION OF THE PREFERRED EMBODIMENTS

In accordance with the present invention, novel toroidal-spiral particles (TSPs) were prepared and therapeutic agents were encapsulated, or entrapped or loaded, in the TSPs, either by self-loading or by incubation. The width of the channels of a TSP can be varied from about 100 nm to about 10 μm, depending on the physico-chemical conditions used to prepare the particles. The release profiles of different proteins and peptides were similar, and independent of the pore size of the polymer matrix.

In accordance with the present invention, self-assembled polymeric particles with novel toroidal-spiral internal channels useful for a targeted delivery and a controlled release of therapeutic agents, like proteins, peptides, and small molecule drugs, and topically effective agents were prepared. In the self-assembly process, droplets of a molten polymer or polymer solution were allowed to settle or rise through a miscible bulk solution. Because interfacial tension is negligible or absent, viscous forces act unhindered on the miscible drops (i.e., drops without capillary interfaces) to form an intricately wound toroidal-spiral structure. When using an aqueous solution of a suitable polymer as the drop phase, the toroidal-spiral shape can be solidified by UV-triggered crosslinking.

Upon introduction into the second liquid, drops of the polymer melt or solution form a characteristic bell shape or vortex ring that is unstable during the subsequent sedimentation, or settling, of the polymer drop through the second liquid by gravity (or centrifugation) because of the absence of a capillary (i.e., two-phase) interface which would inhibit a change in shape. Sedimentation of the drop is characterized by the dimensionless Reynolds number Re, which represents a ratio of inertial to viscous forces, and is calculated as follows:

$$\frac{\text{settling velocity} \times \text{diameter} \times \text{density}}{\text{viscosity}}.$$

Figure 1A:
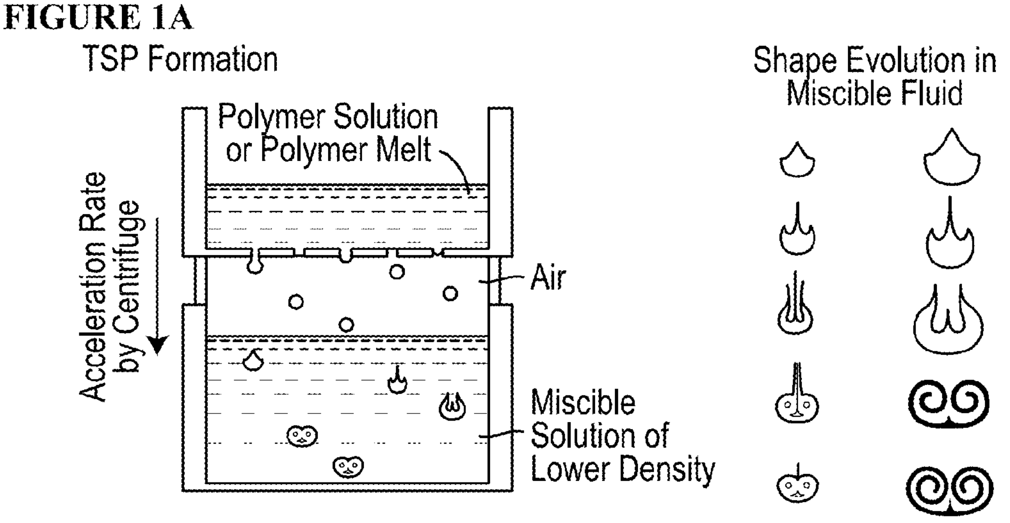
FIG. 1A-1C is a schematic illustrating (a) TSP formation (FIG. 1A), including (b) active agent (e.g., protein) encapsulation (FIG. 1B) and (c) active agent (e.g., protein) release (FIG. 1C)
Figure 1B:
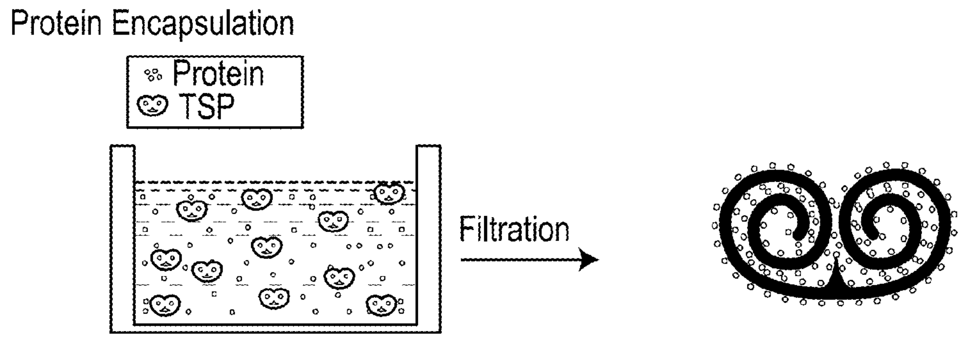
Figure 1C:
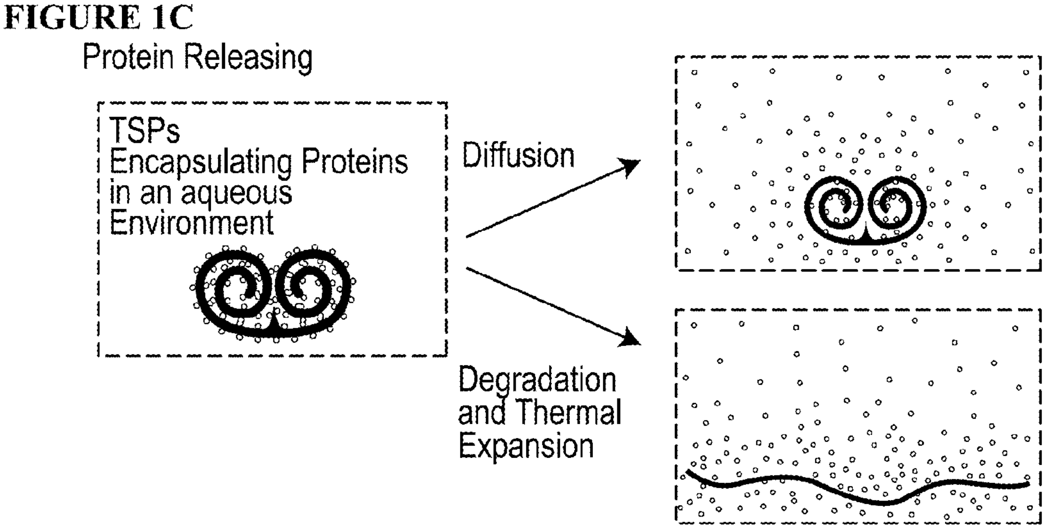

As each drop descends through the second liquid in low Reynolds number flow (Re<0.1) or moderate Reynolds number flow (0.1<Re<300), the drop deforms and rolls up into a toroidal spiral (FIG. 1). This process entrains the surrounding second liquid, including any active agent present in the second liquid, i.e., self-loads the TSP with active agent during manufacture. At a predetermined time or height, the polymer of the TSP is crosslinked either chemically (e.g., with divalent cations) or photochemically (e.g., UV light) to solidify the liquid polymer and provide a TSP structure loaded with an active agent, and having a high surface to volume ratio.

The present TSPs are formed and loaded with proteins entirely within the aqueous phase under flexible temperature and benign conditions (e.g., low shear and low interfacial tension) that preserve delicate macromolecular conformations, and thereby maximize bioactivity and bioavailability. The resultant spiral structure allows for both high drug loadings and prolonged release profiles. The encapsulated proteins are released through the channels of the TSP, which is much different from the typical diffusion-based release through a polymer matrix. TSP channels were from about 1 μm to about 10 μm, which is much larger than the radius of gyration (Rg) of the protein molecules (about 10 nm). Therefore, with known diffusivities of the active agents (and, depending on the system used, the diffusivity and viscosity of the entrained liquid solution as a function of composition), and, the release profiles of the proteins can be predicted and a low amount of protein remains trapped in the particles.

Current methods of preparing particles and therapeutic aerosols (e.g., emulsions, double emulsions, spray drying, supercritical anti-solvent process) involve two- or three-phase systems and temperature changes. These methods have several limitations, including (a) low loading efficiency, (b) reduced biological activity caused by protein denaturation, (c) process complexity and difficulty in scale-up, and (d) non-constant release rates of active agents.

In contrast, the present process and TSP technology offers the advantages of (a) self-assembly in a single liquid phase (aqueous or non-aqueous), thereby avoiding harmful solvents and water-oil interfaces, (b) sustained release of active agents by diffusion from the spiral structure or degradation of the TSP, (c) optional entrainment of active agents during the TSP formation process, and (d) benign process conditions (e.g., temperature) to avoid damage/denaturation of fragile active agents, such as proteins and oligonucleotides.

Figures 2A, 2B, 2C, 2D:
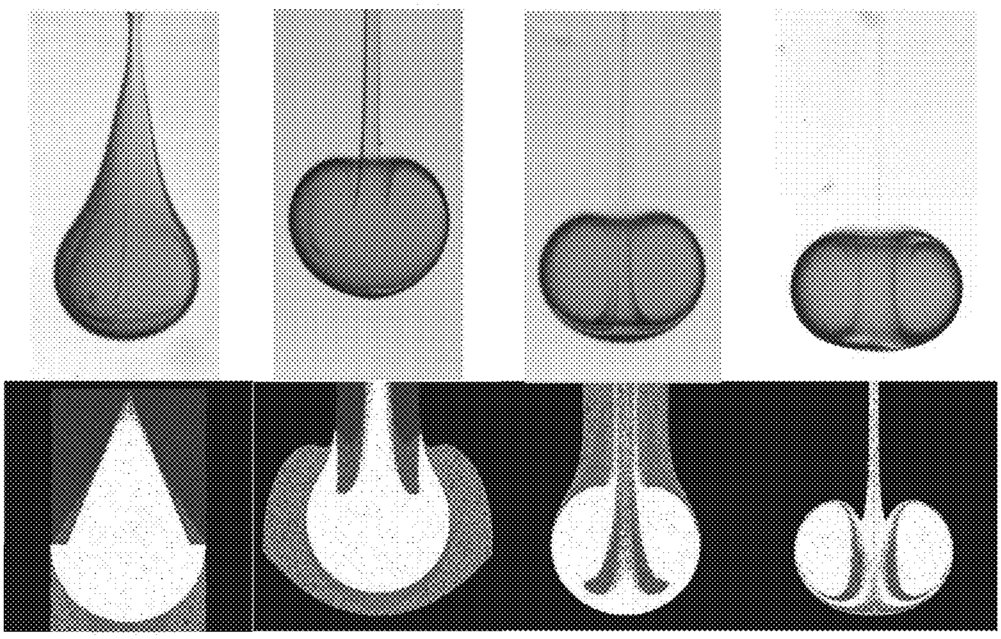
FIG. 2A-2D illustrates the evolution of a sedimentary drop of polyethylene glycol (PEG 700) containing a crosslinking agent, the top figures are high-speed camera images and the bottom figures are computer simulations.

The first step in the self-assembly of TSPs is the formation of toroidal-spiral structures in an aqueous or non-aqueous phase in which a polymer drop is soluble (29, 30). FIG. 2 shows the configurational evolution of a sedimenting drop of a polyethylene glycol (molecular weight of 700) (PEG 700) containing a crosslinking agent (IRGACURE® 2959). The top figures of FIG. 2 are high-speed camera images, and the bottom figures are computer simulations. Regardless of whether a first polymer-containing liquid drop is either introduced below the surface of a second liquid of lower viscosity or splashes onto the second liquid surface, the drop of the first liquid forms a characteristic bell shape upon entering a soluble second liquid of lower (or higher) density (FIG. 2*a*). The fluted elongation at the top (or bottom) of the drop gets drawn into a long tail, which becomes increasingly thinner as the drop continues to settle (or rise). A depression region forms near the rear stagnation point, which deepens around the axis of symmetry and progresses to the front as a second, coaxial tail forms and pulls itself up around the original tail (FIG. 2*b*). Eventually, the tail narrows into a thread and breaks off. Simultaneous with the dynamics of the tail, the bulk of the drop slowly develops a mushroom shape (FIG. 2*c*) with evacuation of the center and entrainment of the second liquid (including any dissolved therapeutic agents such as proteins or peptides, in the case of self loading), followed by a toroidal-spiral shape. The therapeutic agent therefore becomes entrained inside the formed channels.

This cascade of successive drop shapes can be the result of an interaction between the viscous and gravitational forces in the liquids, i.e., a pure shape instability instigated by the initial configuration (i.e., bell shape or vortex ring) of the drop. It was found that various non-dimensional numbers, such as viscosity ratio, Reynolds number (Re), Weber number (We), Peclet number (Pe), and Damkohler number (Da) can be used, alone or in combination, to control the structure of the TSP channels.

An important aspect of the present invention is the progression of initial shape (bell or vortex ring) to the toroidal-spiral shape of the mushroom stage (FIG. 2*c*). The dynamically evolving flow pattern winds up the interface into a toroidal roll, thereby entraining an active agent from behind.

It is theorized, but not relied upon, that a toroidal spiral forms because absent a capillary interface, for which interfacial tension would compete with viscous deforming forces to restore a spherical shape, a perfect sphere is the only (meta)stable shape for a miscible (i.e., soluble) drop. During sedimentation, the drop represents a region of greater density than the surrounding liquid upon which gravity acts. According to the Stokes equations governing viscous-dominated flow, any roughly globular localization of body force produces an envelope of closed streamlines when viewed in a reference frame that descends with the drop. For a perfect sphere, this stream envelope exactly coincides with the interface, according to the classical Hadamard Rybczynski solution in Stokes flow (31, 32). Thus, the toroidal vortex circulates fluid within the drop, while the surrounding liquid streams by without crossing the interface. Any perturbation upsets this delicate, metastable balance between drop shape and the flow pattern.

For the initial bell or vortex-ring shape, the closed stream envelope is not spherical, but has two important features. First, some streamlines cut through the surface of the drop at the rear, thereby entraining liquid, sweeping out the drop from the centre, and forming the ring. Second, the drop extends at least partly outside the envelope toward the front and sides, and the associated liquid volume gets swept to the rear by the liquid passing by, causing the coaxial tail. The first effect entrains the active agent and/or crosslinking agent within the drop. The toroidal vortex winds up the (miscible) interface into a spiral structure (FIG. 2*c,d*).

The polymer comprising the TSPs, either unloaded or loaded with an active agent, typically is crosslinked, either chemically, e.g., a polyvalent solvent or multifunctional organic compound, or by the application of ultraviolet (UV) light.

Various embodiments of the invention include, but are not limited to, (a) water-soluble polymer crosslinked in aqueous solution with a salt, (b) water-soluble polymer crosslinked in aqueous solution with light, (c) oil-soluble polymer crosslinked in oleic solution with light, (d) molten polymer hardened by quenching, and (e) molten polymer sedimenting in a hot-to-cold temperature-gradient (bottom cold, top hot).

Crosslinked TSPs on the millimeter scale, wherein convective effects dominate self-assembly, have been prepared. Scaling calculations show that suitable conditions, as partially described by the dimensonless Reynolds, Weber, Peclet and Domkohler numbers, can mitigate diffusion to enable a liquid self-assembly process down to the micron scale. Studies of the uptake and release of active agents by TSPs have also been performed. It is envisioned that TSPs having a size of about 10 μm to about 10 cm can be prepared. In preferred embodiments, the TSPs have a size of about 10 μm to about 10 mm, and more preferably about 10 μm to about 5 mm.

Millimeter-sized TSPs using poly(ethylene glycol) (PEG) under normal gravity have been prepared. The effects of fluid properties (such as viscosity ratio of the polymer droplets to the miscible second liquid), initial conditions (such as the initial bell shape of the droplets), and crosslinking kinetics were tested to determine the effects on forming TSPs. More particularly, PEG 700 was used to demonstrate the formation of TSPs. The radius of the drops and the radius of the particles were about 1 mm. Smaller particles also can be made. The polymer can be one of many other polymers, examples of which are listed below.

Self-Assembly of Toroidal-Spiral Particles

A drop of PEG 700 mixed with the photoinitiator IRGACURE® 2959 was dripped into water. During sedimentation of the drop, a UV lamp was used to crosslink the PEG and form a solid particle. Scanning electron microscope and light photographs show the multi-layer, spiral structure of the particle, which is essential to encapsulate an active agent during TSP preparation and to allow slow release the active agent by diffusion.

Figure 3:
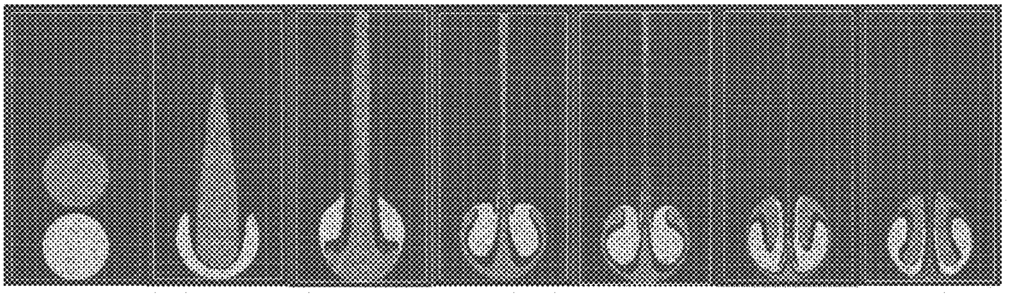
FIG. 3 shows successive stages of the computer-simulated shape evolution of two sedimenting, miscible drops as they coalesce and mix together.
Figure 4:
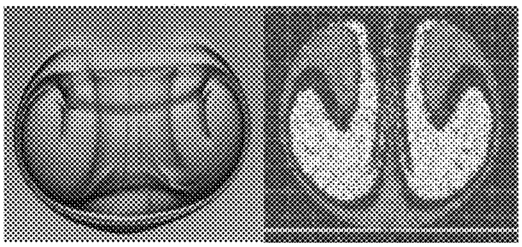
FIG. 4 shows a toroidal-spiral drop after two drops have coalesced and mixed. Left image: laboratory visualization using a high-speed camera. Right image: computer simulation.

In another embodiment two or more drops of polymer are introduced into the second liquid and undergo sedimentation in sufficiently close proximity to each other, e.g., trailing drops, as depicted in FIG. 3, that hydrodynamic interactions between them significantly alter their resultant shape evolutions. Such interactions may include, but are not limited to, the drops merging together and/or mixing (FIG. 4) to yield a different variant of the basic toroidal-spiral shape, e.g., wider channels, which may have advantages for use of the resultant TSP.

In yet another embodiment involving two-drop sedimentation, one of the drops is not polymeric and can therefore does not solidify by cross-linking. With reference to FIG. 3, for example, the upper drop could be polymeric while the lower drop would be another miscible liquid, also of higher density than the second liquid through which both drops sediment. The perturbing presence of the lower drop alters the shape evolution of the upper polymeric drop, and leads to a different variant of the basic toroidal spiral shape upon cross-linking the latter. There may be more than one perturbing upper drop.

In yet another embodiment, the perturbing lower drop contains an active agent that becomes entrained inside the polymeric upper drop during sedimentation. Thus, the entrainment self-loading of an active agent can proceed without having to dissolve the active agent throughout the bulk second liquid.

In yet another embodiment, an active agent is applied to a TSP after the particle is formed. In this embodiment, the active agent is present primarily on the surfaces and within the layers of the TSP. In this embodiment, the TSPs are admixed with a solution or dispersion containing the active agent to load the active agent on the TSP.

In yet another embodiment, one or more first active agent is self-loaded into the TSP during manufacture, then one or more second active agent is loaded onto the TSP by diffusion after TSP formation. This embodiment allows a cocktail of active agents to be incorporated into a TSP, with the same or different release rates for self-loaded and diffusion-loaded active agents.

In yet another embodiment one or more first active agent, e.g., a small-molecule drug, is premixed into the precursor polymer solution before the polymer drop sediments through the second liquid. One or more second active agent, e.g., protein or peptide, that was predissolved in the second liquid then becomes entrained in the toroidal spiral passages during sedimentation. The resultant crosslinked TSP contains the second active agent inside the toroidal-spiral passages, while the first active agent is contained throughout the polymer matrix. This embodiment allows a cocktail of active agents to be incorporated into different portions of a TSP, with different release rates for the protein/peptide versus small molecule active agents.

Figures 5A, 5B:
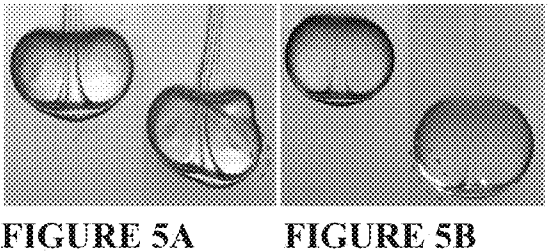

It is preferred to have fast crosslinking reaction kinetics and slow molecular diffusion (i.e., large Pe and large Da) for the TSPs to maintain the internal channeled structures. The weight ratio of PEG 700 to IRGACURE® 2959 can be varied to achieve the desired result. High intensity UV light (about 10 $W/cm^2$ to about 19 $W/cm^2$) is used to crosslink the polymer. At too low of a UV intensity, the polymer drops are not solidified sufficiently fast, thereby causing a distortion in shape due to partial crosslinking of the polymer drops (FIG. 5*a*). At too high of a UV intensity, the structure of the polymer drops was fixed essentially instantly due to the fast crosslinking of the polymer drops (FIG. 5*b*).

Figure 6A:
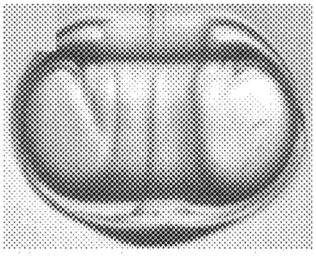
FIG. 6(A)-6(F) are SEM images of TSPs, corresponding to two different stages at which the toroidal-spiral liquid drop shape is crosslinked by UV exposure.
Figure 6B:
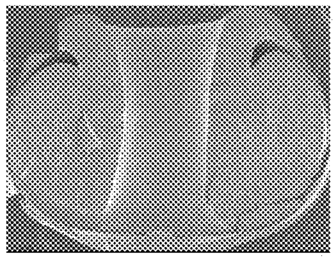
Figure 6C:
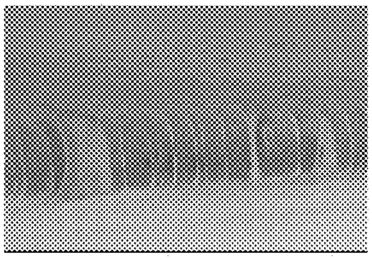
Figure 6D:
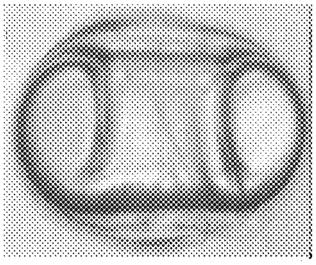
Figure 6E:
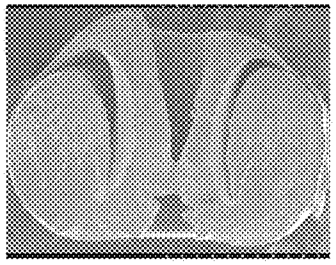
Figure 6F:
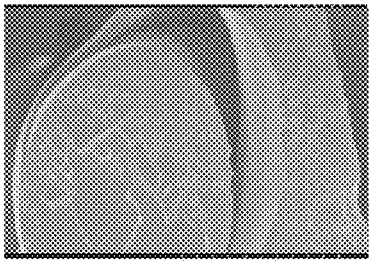
Figure 7A:
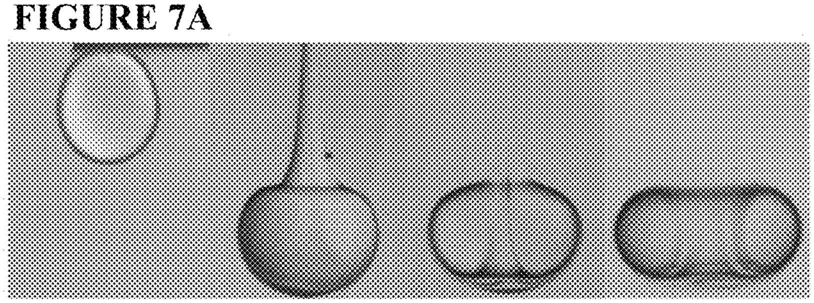
FIG. 7A-7D shows the evolution of sedimenting polymer drops of approximately 2 mm diameter released from various heights to splash through the surface of the bulk solution.
Figure 7B:
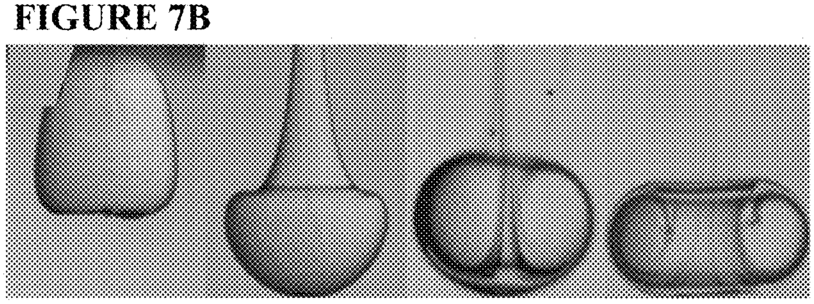
Figure 7C:
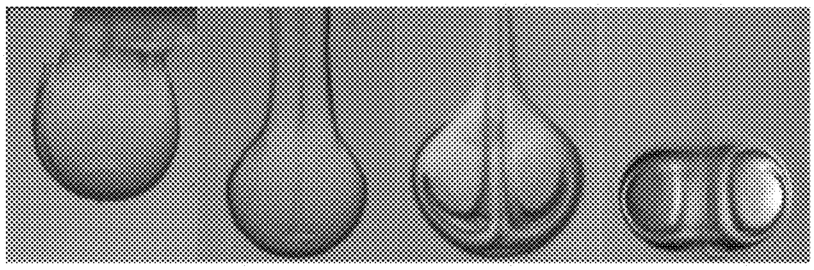
Figure 7D:
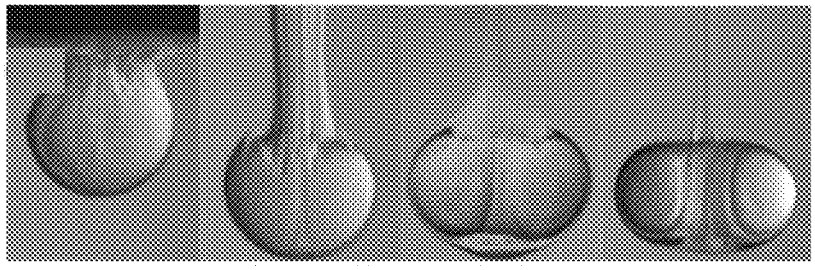
Figure 9A:
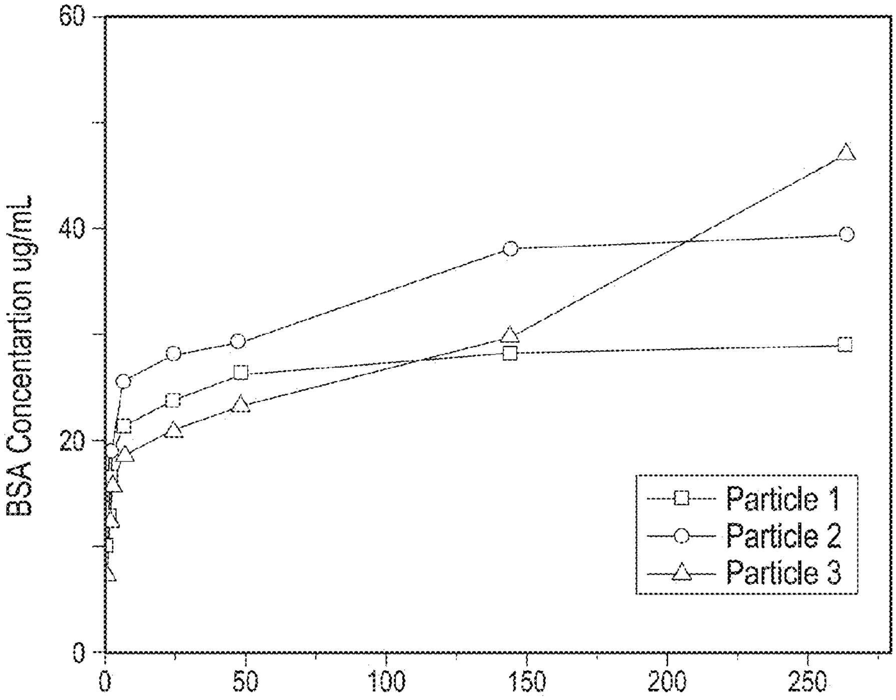
FIG. 9A-9D shows the release kinetics of BSA from self-loaded TSAs over time.
Figure 9B:
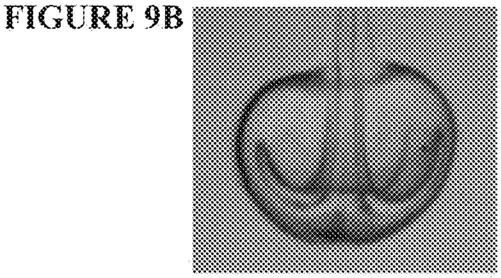
Figure 9C:
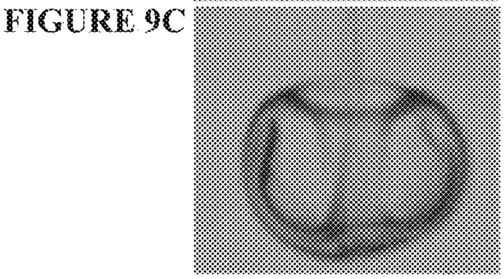
Figure 9D:
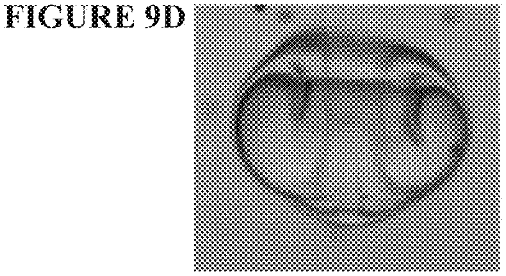

SEM images were taken at two stages of the TSP formation (FIGS. 6*a* and 6*b*). The TSP channels are smooth in FIGS. 6*b*, 6*e*, and 6*f*, indicating either that no crosslinking of the polymer occurred across the channel or that polymer diffusion across the channel was slower than crosslinking reaction. However, at the narrowest part of the channel, polymer diffusion was comparable to the crosslinking reaction. In the SEM image of FIG. 6*c*, a network was formed with micron-size pores. Typically, channel of the TSP have a width of about 100 nm to about 100 μm.

In addition, the channel volume of the TSP, in relation to the total volume of the TSP, is about 5% to about 60%, typically about 5% to about 50%, and more typically about 10% to about 40%.

Effect of Viscosity Ratio

A viscosity ratio of the first drop-forming solution, e.g., a polymer solution, to the second liquid of lower viscosity, i.e., the bulk phase, plays an important role in the formation of TSPs. Studies to determine the effect of droplet rheology by varying the drop/bulk viscosity ratio for Newtonian liquids were performed. Several aqueous solutions of glycerol were used for the drops. Additional studies focused on the non-Newtonian rheology of polymer solutions. At higher glycerol concentrations, the density ratio and the viscosity ratio of the glycerol droplet to the bulk phase increased. Therefore, sedimentation of the drop was faster, and the drop was less susceptible to deformation by the less viscous bulk liquid streaming past the drop. Pictures taken using a high-speed camera show that at higher viscosity ratios, fewer layers formed in the spiral before the Rayleigh-Taylor instability disintegrated the ring into two or more daughter droplets.

It therefore has been found that a viscosity ratio of the polymer drop to the bulk solution of about 0.05 to about 20 generates the TSP structure. In a preferred embodiment, the viscosity ratio is about 15 to 1, or about 10 to 1 or less, e.g., 9 to 1, 8 to 1, 7 to 1, 6 to 1, 5 to 1, 4 to 1, 3 to 1, 2 to 1, or 1 to 1, and all subranges therein. When the viscosity of the polymer drop was too much greater than the viscosity of the bulk solution, the viscous force was not sufficient to generate layered structures, but expanded the drop to a flat ring, then a bowl-shape structure. A reduced viscosity ratio enhances TSP formation and narrow channels were obtained. The combined effects of viscous force, diffusion, and sedimentation influence toroidal-spiral particle/droplet formation, growth, and deceleration. As the Reynolds number and Weber number of the system increase, the range of desirable viscosity ratios decreases, with a preferred ratio of about 3 to 1 to about 1 to 1.

Effect of Initial Velocity

When a polymer droplet falls, its potential energy of altitude is converted into kinetic energy. The kinetic energy of a drop at the moment of impact with the surface of the second liquid is subsequently transferred to bulk motion of the bulk liquid, such as surface waves and motion of the droplets, that are eventually dissipated by viscous forces. Therefore, when polymer droplets enter the bulk solution at different velocities, the initial shape of the drop varies (FIG. 7). Different impact velocities were achieved by setting a drop-forming needle at various heights from the air-bulk solution interface. In particular, FIG. 7 shows that: (a) Drop height of 1 mm produces a characteristic sphere-like initial shape and very thin channels. (b) Drop height of 7 cm produces a characteristic triangle like initial shape and produces wider channels than particles dropped at lower heights. (c) Drop height of 14 cm produces a droplet that spreads over contact area of the surface and falls back onto itself to form a characteristic bell shape. The thickest channel formation is observed at a drop height of 14 cm. (d) Drop height of 18 cm produces a droplet that spreads over contact area of the surface similar to that of 14 cm, but with more waves on the particle and tail. Layer formation at a drop height of 18 cm is similar to that observed at a drop height of 1 mm.

To avoid fragmentation of the droplet due to impact velocity, the velocity criterion is expressed in terms of a relevant dimensionless group. Rather than specifying a particular velocity, the combination of velocity, drop diameter, density, and surface tension, i.e., the TSP preparation conditions, is such that the relevant dimensionless group formed from these variables, i.e., the Weber number (We) (density times square of the velocity times diameter divided by surface tension), preferably is about 0.1 to about 200, and more preferably about 0.1 to about 160, in order to form a cohesive vortex ring upon splashing through surface of the bulk liquid. By having a sufficiently low impact velocity such that surface tension forces to overcome kinetic energy, and thereby inhibit the splashing (breaking apart into smaller drops), the drop remains intact while submerging. More extensive studies with the specific liquids used in each embodiment indicate which range of Weber numbers is preferred for forming a particular TSP. For example, the 18 cm altitude (fourth image, last unfragmented drop) in FIG. 5 corresponds to We=128.

At We<0.1, the droplet could not penetrate through the air-bulk interface although the density of the drop phase fluid was higher than the bulk phase. When We is increased to greater than 0.1, the polymer drop penetrates through the air-bulk interface and the initial bell shape forms. High Weber numbers lead to splashing or ejection rather than the advantageous bell initial shape. At moderate Weber numbers, as opposed to very low Weber numbers, the TSP structure formed faster and the distance between the TSP layers was bigger, which may improve protein self-loading. Therefore, without changing solutions, the easiest way to control the channel size and distance between channels is to vary the kinetic energy of the drops by generating polymer drops at different distances from the surface of the bulk solution (FIG. 7). When the impact kinetic energy is increased, the initial submerged shape varied from a smooth sphere to a more flattened configuration. When the drops entered the interface from 14 cm or higher, there were obvious waves on the drops and tails. The width of the TSP Channels and the distance between the channels became larger with increased kinetic energy of the drops up to a certain limit where when passed, the channel width became smaller.

To provide stable and reproducible TSPs, the self-assembly conditions should be operated at a low Reynolds number, Re=UR/v of less than about 300, e.g., about 0.1 to about 300, wherein U ($m \cdot s^{-1}$) is the velocity of polymer drop sedimentation, R (m) is the radius of the polymer drop, and v ($m^2 \cdot s^{-1}$) is the kinematic viscosity of the bulk solution. A low Re controls the shape of TSP channels in the final TSP. A low Weber number, $We = \rho U^2 R/\sigma < 10$, where $\rho$ ($kg \cdot m^{-3}$) is the density of the polymer drop and $\sigma$ ($N \cdot m^{-1}$) is the surface tension at the interface between the bulk phase and air, also is preferred. At high Reynolds numbers, instability occurs in the sedimenting shape, while high Weber numbers lead to splashing or ejection instead of an advantageous initial bell shape. At moderate Weber numbers, as opposed to very low Weber numbers, the TSP formed faster and the distance between the TSP layers was larger, which can benefit protein self-loading.

Embodiments of the invention are not be restricted to very low values of the Reynolds number, e.g., Re<0.1. Operation at a moderate Reynolds number (0.1<Re<300) may alter the resultant spiral shape due effects of liquid inertia (compared to viscosity).

Therefore, without changing the drop solution or the bulk solution, a facile way to control channel size and distance between channels is to vary the kinetic energy of the drops by generating polymer drops at different distances from the surface of the bulk solution. The width of the TSP channels and the distance between the channels became larger with increased kinetic energy of the drops up to a limit that, when passed, the channel width became smaller.

High-speed camera images show that a drop height of 1 mm produces a characteristic sphere like initial shape and very thin channels. A drop height of 7 cm produces a characteristic triangle like initial shape and produces wider channels than particles dropped at lower heights. A drop height of 14 cm produces a droplet that spreads over the contact area of the surface, and falls back onto itself to form a characteristic bell shape. The thickest channel formation was observed at a drop height of 14 cm. A drop height of 18 cm produces a droplet that spreads over the contact area of the surface similar to that of 14 cm, but with more waves on the particle and tail. Layer formation at a drop height of 18 cm is similar to that observed at a drop height of 1 mm.

A TSP also can be loaded with two or more active agents by using a combination of diffusion-loading and self-loading, or by using more than one active agent either in the diffusion-loading or self-loading step.

Generating Micro-Size Toroidal-Spiral Particles by High Acceleration Rate

The TSP production process proceeds by viscous evolution of a Rayleigh instability in a single phase flow in the absence of significant interfacial tension, as opposed to a multi-phase flow, in which interfacial tension tends to dominate over volumetric forces for micro-scale droplets. The mechanism of TSP self-assembly is theorized to involve interaction and competition between various physicochemical processes and parameters: (a) viscous-dominated flow of soluble polymer drops, (b) diffusion, (c) a crosslinking chemical or photoinitiated reaction, (d) initial shapes of the drops upon splashing into the bulk solution (influenced by kinetic energy upon impact), and (e) viscosity ratios between droplet phases and the bulk phase.

Producing micron-size droplets and particles has been challenging in the past. Emulsification methods are most plentiful. Emulsification methods use surfactants and high-energy dissipation turbulence to enhance drop breakup, especially when droplets are micro- or nanoscale and surface tension dominates over the body forces. By this process, little control over the formation of individual droplets is available, and the size distribution of the droplets is broad. "Flow focusing" in microchannels generates droplets down to 10 microns. This "bottom-up" approach can be used at the level of individual drops, and droplet size is related to flow rates.

In the preparation of a TSP, the formation of a toroidal-spiral structures is related to the initial condition of the droplets and competitive kinetics. The flow of the droplet through a second bulk liquid phase is relatively low Reynolds number Stokes flow, i.e., inertia effects are weak compared to viscosity effects. Similar to millimeter-sized drops, an axisymmetric bell-shaped microdroplet is envisioned to undergo the torus/breakup transformation. The number of layers formed in a TSP within predetermined distance/time parameters is related to initial drop shapes and the viscosity ratio of the droplet phase to the bulk phase.

Additional embodiments (aside from gravitational sedimentation of the polymer drop) include centrifugation to increase the effective g-force driving sedimentation (or buoyant rise) of the polymer drops, and thereby attain desired parameters for the small lengthscale of TSPs.

Characterizing the Sizes and Morphologies of the Particles

The shape of the TSPs and their inner toroidal-spiral structure can be observed by various microscopies. For example, the size and shape of the TSPs can be analyzed using Scanning Electron Microscopy (SEM). Two methods can be applied to obtain the inner structures of the TSPs, i.e., confocal microscopy and dissected particles by SEM. Fluorescent dyes also can be blended with the polymer solution or melt to provide a contrast for confocal microscopy. Depending on the focal distance of the microscopy, a structure of a few hundred nanometers can be observed. The TSPs also can be dissected by microtome, a mechanical instrument traditionally used to cut biological specimens into sections, and the structure can be confirmed by SEM.

Examples of Proteins and Polymers

Therapeutic proteins, peptides, and small molecule drugs can be loaded onto a present TSP. The identity of a small molecule drug is not limited, as long as the small molecule drug is soluble in the bulk phase for self-loading or can be loaded onto the TSP through diffusion. The small molecule drug also must be chemically compatible with the polymer forming the TSP and the bulk liquid. Persons skilled in the art can readily determine which small molecule drugs can be incorporated into a present TSP after the polymer drop and bulk liquid are identified.

Nonlimiting examples of therapeutic proteins that can be loaded onto a present TSP are listed in the following table. The molecular weight of the proteins can vary from about 1 kDa (kiloDalton) to more than 100 kDa, e.g., 200 kDa. Delivery technologies for these proteins represent the general challenges of targeted, sustained release of therapeutic proteins.

The TSPs are loaded with an active agent either during the process of manufacture of the TSP, or after the TSP has been prepared. As used herein, the term "loaded TSP" refers to a TSP having an active agent incorporated therein or added thereto. Loading of the active agent includes one or more of impregnating, imbedding, entrapping, absorbing, and adsorbing of an active ingredient into or onto the TSPs. Loading of the active agent also can be referred to as an "entrapment." The term entrapment refers to a physical loading of the active agent onto and into the TSPs.

An active agent loaded onto or into a TSP is not limited to the three protein drugs disclosed above. The identity of the active agent is not limited, and, for example, can be a therapeutic drug or a topically active agent for use in therapeutic and personal care applications.

An active agent therefore can be a drug. Examples of drugs that are contemplated include, but are not limited to, natural enzymes, proteins derived from natural sources, recombinant proteins, natural peptides, synthetic peptides, cyclic peptides, antibodies, receptor agonists, cytotoxic agents, immunoglobins, beta-adrenergic blocking agents, calcium channel blockers, coronary vasodilators, cardiac glycosides, antiarrhythmics, cardiac sympathomemetics, angiotensin converting enzyme (ACE) inhibitors, diuretics, inotropes, cholesterol and triglyceride reducers, bile acid sequestrants, fibrates, 3-hydroxy-3-methylgluteryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin II receptor antagonists, peripheral vasodilators, antiandrogens, estrogens, antibiotics, retinoids, insulins and analogs, alpha-glucosidase inhibitors, biguanides, meglitinides, sulfonylureas, thizaolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-$HT_4$ partial agonists, antihistamines, cannabinoids, dopamine antagonists, serotonin antagonists, cytoprotectives, histamine H2-receptor antagonists, mucosal protective agent, proton pump inhibitors, *H. pylori* eradication therapy, erythropoi-

TABLE

Examples of Therapeutic Proteins and Growth Factors.

| Protein | Abbreviation | Molecular weight (kDa) | Activities |
|---|---|---|---|
| Transforming growth factor-α | TGF-α | 5.5 | Migration and proliferation of keratinocytes; extracellular matrix synthesis and deposition. |
| Insulin | | 5.8 | Treatment for diabetes. |
| Epidermal growth factor | EGF | 6.2 | Proliferation of epithelial, mesenchymal, and fibroblast cells. |
| Basic fibroblast growth factor | bFGF/FGF-2 | 17.2 | Proliferation of fibroblasts and initiation of angiogenesis |
| Transforming growth factor-β | TGF-β | 25 | Proliferation and differentiation of bone forming cells; chemoattractant for fibroblasts |
| Bone morphogenetic protein | BMP-2, BMP-7 | 26.0 31.5 | Differentiation and migration of bone forming cells |
| Vascular endothelial growth factor | BEGF | 38.2 | Migration, proliferation, and survival of endothelial cells |
| Immunoglobulin G | IgG 150 | | Bind to many pathogens, for example viruses, bacteria, and fungi, and protects the body against them. |

eses stimulants, hematopoietic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-$A_2$ inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptse inhibitors, protease inhibitors, anemia, Kaposi's sarcoma, aminoglycosides, carbapenems, cephalosporins, glycopoptides, lincosamides, macrolides, oxazolidinones, penicillins, streptogramins, sulfonamides, trimethoprim and derivatives, tetracyclines, anthelmintics, amebicies, biguanides, cinchona alkaloids, folic acid antagonists, quinoline derivatives, *Pneumocystis carinii* therapy, hydrazides, imidazoles, triazoles, nitroimidzaoles, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigrane preparations, biological response modifiers, carbamic acid eaters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, antracyclines, actinomycinds, camptothecin derivatives, epipodophyllotoxins, taxanes, vinca alkaloids and analogs, antiandrogens, antiestrogens, nonsteroidal aromatase inhibitors, protein kinase inhibitor antineoplastics, azaspirodecanedione derivatives, anxiolytics, stimulants, monoamind reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g. lidocaine, articaine hydrochloride, bupivacaine hydrochloride), antipyretics, hynotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opoid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, vitamin K analogs and antagonists.

In some embodiments, the drug is a protein, antibody, peptide, or small molecule. In some specific embodiments, the drug is neocarzinostatin, zinostatin, adenosine deaminase, asparaginase, interferon α2b, interferon α2a, growth hormone receptor agonist, granulocyte colony-stimulating factor (G-CSF), anti-vasco endothelial growth factor (VEGF) aptamer, anti-tumor necrosis factor (TNF) Fab, diFab antibody, doxorubicin, doxorubicin-galactosamine, camptothecin, paclitaxel, a platinate, erythropoietins, Factor H, Factor VIII (FVIII), von Willebrand Factor (vWF), Factor VIIa (FVIIa), or Factor IX (FIX). (See, e.g., Pasut et al. *Prog. In Polymer Science,* 2007, 32, 933-961, which is incorporated herein by reference in its entirety.) In other embodiments, the drug is a plasma protein or blood coagulation factor such as, for example, erythropoietin, Factor H, Factor VIII (FVIII), von Willebrand Factor (vWF), Factor VIIa (FVIIa), Factor IX (FIX) and the like.

With respect to topically active agents, a compound for loading onto the TSP can be any of a wide variety of compounds, either water soluble or oil soluble. A composition containing a present TSP, therefore, can be applied to a substrate, like the skin or hair, and the active agent then performs its intended function.

The active agent can be a water-soluble or water-dispersible compound, i.e., is hydrophilic. The active agent also can be oil soluble or oil dispersible, i.e., is hydrophobic.

The active agent, therefore, can be one of, or a mixture of, a cosmetic compound, a medicinal compound, or any other compound that is useful upon topical application to the skin, or hair. Such active agents include, but are not limited to, skin care compounds, antibacterial compounds, antifungal compounds, antiacne agents, antiinflammatory compounds, pharmaceuticals, topical anesthetics, sunscreens, an insect repellant, fluorescent compounds, optical brighteners, and other cosmetic and medicinal topically effective compounds. The quantities of such active agents present in the TSPs are sufficient to perform their intended function, without adversely affecting the benefits of other ingredients present in the composition.

For example, a skin conditioner can be the optional active agent in a delivery system of the present invention. Skin conditioners include, but are not limited to, humectants, such a fructose, glucose, glycerin, propylene glycol, glycereth-26, mannitol, and urea, pyrrolidone carboxylic acid, hydrolyzed lecithin, coco-betaine, cysteine hydrochloride, glucamine, PPG-15, sodium gluconate, potassium aspartate, oleyl betaine, thiamine hydrochloride, sodium laureth sulfate, sodium hyaluronate, hydrolyzed proteins, hydrolyzed keratin, amino acids, amine oxides, water-soluble derivatives of vitamins A, E, and D, silicones, amino-functional silicones, ethoxylated glycerin, alpha-hydroxy acids and salts thereof, triglycerides, fatty oil derivatives, such as PEG-24 hydrogenated lanolin, almond oil, grape seed oil, and castor oil, and mixtures thereof. Numerous other skin conditioners are listed in the *CTFA Cosmetic Ingredient Handbook, Tenth Ed.*, T. E. Gottshalck et al, ed., The Cosmetic, Toiletry and Fragrance Association (2004), (hereafter CTFA Handbook), pages 2392-2395, incorporated herein by reference.

If the composition is intended to be a sunscreen, then compounds such as benzophenone-3, trihydroxycinnamic acid and salts, tannic acid, uric acids, quinine salts, dihydroxy naphtholic acid, an anthranilate, diethanolamine methoxycinnamate, p-aminobenzoic acid, phenylbenzimidazole sulfonic acid, PEG-25, p-aminobenzoic acid, or triethanolamine salicylate can be used as the active agent.

Further, sunscreen compounds such as dioxybenzone, ethyl 4-[bis(hydroxypropyl)] aminobenzoate, glyceryl aminobenzoate, homosalate, methyl anthranilate, octocrylene, octyl methoxycinnamate, octyl salicylate, oxybenzone, padimate O, red petrolatum, titanium dioxide, 4-menthylbenzylidene camphor, benzophenone-1, benzophenone-2, benzophenone-6, benzophenone-12, isopropyl dibenzoyl methane, butyl methoxydibenzoylmethane, octocrylene, or zinc oxide can be used as the active agent. Other sunscreen compounds are listed in CTFA Handbook, pages 2397-2399, incorporated herein by reference.

Similarly, active agents, like antifungal compounds, antibacterial compounds, anti-inflammatory compounds, topical anesthetics, skin rash, skin disease, and dermatitis medications, and anti-itch and irritation-reducing compounds can be used as the active agent in compositions of the present invention. For example, analgesics such as benzocaine, dyclonine hydrochloride, aloe vera, and the like; anesthetics such as butamben picrate, lidocaine hydrochloride, xylocaine, and the like; antibacterials and antiseptics, such as povidone-iodine, polymyxin b sulfate-bacitracin, zinc-neomycin sulfate-hydrocortisone, chloramphenicol, ethylbenzethonium chloride, erythromycin, and the like; antiparasitics, such as lindane; essentially all dermatologicals, like acne preparations, such as benzoyl peroxide, erythromycin, clindamycin phosphate, 5,7-dichloro-8-hydroxyquinoline, and the like; antiinflammatory agents, such as alclometasone dipropionate, betamethasone valerate, and the like; burn relief ointments, such as o-amino-p-toluenesulfonamide monoacetate, and the like; depigmenting agents, such as monobenzone; dermatitis relief agents, such as the active steroid amcinonide, diflorasone diacetate, hydrocortisone, and the like; diaper rash relief agents, such as methylbenzethonium chloride, and the like; emollients and moisturizers, such as lanolin oil, petrolatum, mineral wax, and the like; fungicides, such as butocouazole nitrate, haloprogin, clotrimazole, and the like; herpes treatment drugs, such as O-[(2-hydroxymethyl)-methyl]guanine; pruritic medications, such as alclometasone dipropionate, betamethasone valerate, isopropyl myristate MSD, and the like; psoriasis, seborrhea, and scabicide agents, such as anthralin, methoxsalen, coal tar, and the like; steroids, such as 2-(acetyloxy)-9-fluoro-1',2',3',4'-tetrahydro-11-hydroxypregna-1,4-dieno-[16,17-b]naphthalene-3,20-dione and 21-chloro-9-fluoro-1',2',3',4'-tetrahydro-11b-hydroxypregna-1,4-dieno-[16,17-b]naphthalene-3,20-dione. Any other medication capable of topical administration, like skin bleaching agents, skin protestant, such as allantoin, and antiacne agents, such as salicylic acid, also can be incorporated in a composition of the present invention in an amount sufficient to perform its intended function. Other topically active compounds are listed in Remington's Pharmaceutical Sciences, 17th Ed., Merck Publishing Co., Easton, Pa. (1985), pages 773-791 and pages 1054-1058 (hereinafter Remington's), incorporated herein by reference.

The active agent also can be a plant extract on a natural oil. Nonlimiting plant extracts are those obtained from alfalfa, aloe vera, amla fruit, angelica root, anise seed, apple, apricot, artichoke leaf, asparagus root, banana, barberry, barley sprout, bee pollen, beet leaf, bilberry fruit, birch leaf, bitter melon, black currant leaf, black pepper, black walnut, blueberry, blackberry, burdock, carrot, cayenne, celery seed, cherry, chickwood, cola nut, corn silk, cranberry, dandelion root, elderberry, eucalyptus leaf, flax oil powder, ginger root, gingko leaf, ginseng, goldenrod, goldenseal, grape, grapefruit, guava, hibiscus, juniper, kiwi, kudzu, lemon, licorice root, lime, malt, marigold, myrrh, olive leaf, orange fruit, orange peel, oregano, papaya fruit, papaya leaf, passion fruit, peach, pear, pine bark, plum, pomegranate, prune, raspberry, rice bran, rhubarb root, rosemary leaf, sage leaf, spearmint leaf, St. John's wart, strawberry, sweet cloves, tangerine, violet herb, watercress, watermelon, willow bark, wintergreen leaf, witch hazel bark, yohimbe, and yucca root.

The active agent further can be a fluorescent compound. Examples of fluorescent compounds include, but are not limited to, a distyrylbiphenyl derivative, stilbene or a stilbene derivative, a pyralozine derivative, or a coumarin derivative. The optional brightener typically is a derivative of stilbene or 4,4'-diaminostilbene, biphenyl, a 5-membered heterocycle, e.g., triazole, oxazole, or imidazole, or a 6-membered heterocycle, e.g., a coumarin, a naphthalamide, or an s-triazine.

The optical brighteners are available under a variety of tradenames, such as TINOPAL®, LEUCOPHOR®, and CALCOFLUOR®. Specific fluorescent compounds include, but are not limited to, TINOPAL® 5BM, CALCOFLUOR® CG, and LEUCOPHOR® BSB.

The loaded TSPs can be added directly to a composition. In some embodiments, a need also may exist to ensure that leakage of an active agent from a TSP into the formulation is avoided. In this case, a barrier layer can be applied to the loaded TSPs by applying a coating material to the loaded TSPs.

A number of different coating materials can be used as a barrier layer, including, but not limited to, low melting alcohols ($C_8$ through $C_{20}$) and fatty alcohols ethoxylated with one to three moles of ethylene oxide. Examples of fatty alcohols and alkoxylated fatty alcohols include, but are not limited to, behenyl alcohol, caprylic alcohol, cetyl alcohol, cetaryl alcohol, decyl alcohol, lauryl alcohol, isocetyl alcohol, myristyl alcohol, oleyl alcohol, stearyl alcohol, tallow alcohol, stearety-2, ceteth-1, cetearth-3, and laureth-2. Additional fatty alcohols and alkoxylated alcohols are listed in the *International Cosmetic Ingredient Dictionary and Handbook, Tenth Edition, Volume* 3, pages 2127 and pages 2067-2073 (2004), incorporated herein by reference.

Another class of materials that can be used in a barrier layer is the $C_8$ to $C_{12}$ fatty acids, including, but not limited to, stearic acid, capric acid, behenic acid, caprylic acid, lauric acid, myristic acid, tallow acid, oleic acid, palmitic acid, isostearic acid, and additional fatty acids listed in the *International Cosmetic Ingredient Dictionary and Handbook, Tenth Edition*, Volume 3, pages 2126-2127 (2004), incorporated herein by reference.

The barrier material also can be a hydrocarbon, like mineral oil, 1-decene dimmer, polydecene, paraffin, petrolatum, vegetable-derived petrolatum, or isoparaffin. Another class of barrier materials is waxes, like mink wax, carnauba wax, and candelilla wax, for example, and synthetic waxes, like silicone waxes, polyethylene, and polypropylene, for example.

Fats and oils can be useful barrier material agents, which include, for example, but are not limited to, lanolin oil, linseed oil, coconut oil, olive oil, menhaden oil, castor oil, soybean oil, tall oil, rapeseed oil, palm oil, and neatsfoot oil, and additional fats and oils listed in the *International Cosmetic Ingredient Dictionary and Handbook, Tenth Edition, Volume* 3, pages 2124-2126 (2004). Other useful classes of barrier materials include a water-insoluble ester having at least 10 carbon atoms, and preferably 10 to about 32 carbon atoms. Numerous esters are listed in *International Cosmetic Ingredient Dictionary and Handbook, Tenth Edition, Volume* 3, pages 2115-2123 (2004).

A coating material can be present on the loaded TSPs in an amount of about 5% to about 70%, based on the weight of the loaded TSP. In a more preferred embodiment, the amount of the coating material is about 10% to about 50%, and even more preferably about 20% to about 50 wt. %, based on the weight of the loaded TSPs.

The present TSPs typically are formulated into compositions designed for therapeutic use or personal care use, for example. The compositions of the present invention containing a TSP therefore can be formulated with optional ingredients traditionally included in cosmetic, personal care, medicinal, and other such compositions. These optional ingredients include, but are not limited to, fragrances, preservatives, antioxidants, detackifying agents, and similar types of compounds. The optional ingredients are included in the composition in an amount sufficient to perform their intended function.

A further aspect of the invention is directed to a pharmaceutical composition that includes TSPs of the present invention loaded with a drug, together with a pharmaceutically acceptable excipient, such as a diluent or carrier. Pharmaceutical compositions suitable for use in the present invention include those wherein the TSPs are administered in an effective amount to achieve its intended purpose. Administration of the TSPs can be via any route, such as oral, injection, inhalation, and subcutaneous. The formulation can be a liquid, aerosol, suspension, tablet, capsule, microcapsule, and the like.

Suitable pharmaceutical formulations can be designed by the skilled artisan depending on the route of administration and the desired dosage. See, e.g., Remington's Pharmaceutical Sciences, 1435-712 (18th ed., Mack Publishing Co, Easton, Pa., 1990). Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the pharmacokinetic data obtainable through animal or human clinical trials.

The phrase "pharmaceutically acceptable" refers to compounds and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active agents also can be incorporated into the compositions. Such supplementary active agents are not loaded onto the TSPs.

Three nonlimiting polymers initially were used to prepare TSPs. Solutions of these polymers have a wide range of viscosities and crosslink by different mechanisms.

Alginic acid (AA) is a polysaccharide having two repeating monomer acids units. Crosslinking of AA and sodium alginate (SA) to a gel is achieved by the presence of polyvalent cations, and preferably divalent cations, such as calcium ions ($Ca^{2+}$), which are coordinated with carboxylate groups of alginate into a tetradentate structure (33). The gel dissolves after the release of divalent ions in solution (34). Aqueous solutions of AA and SA are highly viscous, even at moderate concentrations, because of the high molecular weight of AA.

Poly(ethylene glycol) (PEG) is commonly used as a drug delivery system because of its biocompatibility and prevention of non-specific protein absorption (36-38). Commonly employed PEG hydrogels can be formed through photo- or thermal-polymerization of PEG diacrylate (PEG-DA) with or without comonomers, such as acrylic acid, acrylamide, and allylamine (34-36). The viscosity of the PEG aqueous solutions covers a wide range based on the molecular weight and concentration of PEG.

Poly(D,L-lactide-co-glycolide) (PLGA) is a biodegradable polymer used for drug delivery and is approved by the Food and Drug Administration (FDA). It is insoluble in water, but soluble in water-miscible organic solvents. Addition of water to a solution of PLGA dissolved in a water-miscible organic solvent causes precipitation of PLGA and formation of solid particles. The viscosity of PLGA solutions is related to solvent viscosity and the molecular weight of PLGA.

| Polymer | Crosslinking mechanism | Viscosity | Release mechanism |
|---|---|---|---|
| Sodium Alginate (SA) | Divalent ions crosslinking | High viscosity (e.g., about 250 cp for 2% SA in water) | Diffusion and gel dissolution |
| Poly (ethylene glycol) diacrylate (PEG-DA) | Photo- and thermal-polymerization | Large range of viscosity due to the molecular weight and concentration | Diffusion |
| Poly(D,L-lactide-coglycolide (PLGA) | Hydrophobic interaction | A range of viscosity due to the viscosity due to the viscosity of organic solvent and molecular weight of PLGA | Diffusion and erosion |

The process to generate the TSPs is self-assembly, which is easily scaled up. Overall, this system allows producing three-dimensional drug carriers and releasing molecules in a sustainable and high efficient way.

A polymer utilized to prepare a present TSP is not limited to the three polymers disclosed above. The identity of the polymer is not limited, except a melt or solution of the polymer must be soluble in the second bulk phase liquid. The polymer can be hydrophilic or hydrophobic. Typically, the polymer is a water-soluble or water-dispersible polymer.

A "water soluble or water-dispersible polymer" refers to a hydrophilic, non-peptidic homopolymer or copolymer. The term "water soluble or water-dispersible polymer" includes linear or branched polymers such as poly(alkylene glycol), water soluble polyphosphazenes or carbohydrate-based polymers such as polysaccharides. The water soluble or water-dispersible polymer can also be end-capped. Non-limiting examples of water soluble or water-dispersible polymers contemplated include polyethylene glycol (PEG), branched PEG, polysialic acid (PSA), polysaccharides, pullulane, chitosan, hyaluronic acid, chondroitin sulfate, dermatan sulfate, starch, dextran, carboxymethyl-dextran, polyalkylene oxide (PAO), copolymers of polyalkylene oxides, polyoxamer (such as PLURONIC®), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyethylene-co-maleic acid anhydride, polystyrene-co-maleic acid anhydride, poly(1-hydroxymethylethylene hydroxymethylformal) (PHF), and 2-methacryloyloxy-2'-ethyltrimethylammonium phosphate (MPC). The molecular weight of the water soluble or water dispersible polymer is at least 200 g/mol, with no upper limit.

In other embodiments, the water soluble polymer is a PEG, which can be linear or branched. In some embodiments, the water soluble polymer is a block polymer of PEG and other poly(alkylene glycol), such as PLURONIC® F127 or PLURONIC® F68.

Additional polymers useful in the present invention include, but are not limited to:

Poly alkyl (acrylates):
Poly(benzyl acrylate)
Poly(benzyl a-ethyl acrylate)
Poly(benzyl α-propyl acrylate)
Poly(cyclohexyl methacrylate)
Poly(ethyl acrylate)
Poly(isopropyl acrylate)
Poly(ethyl methacrylate)
Poly(ethyl α-ethyl acrylate)
Poly(ethyl α-propyl acrylate)
Poly(fluorescein O-methacrylate)
Poly(glycidyl methacrylate)
Poly(hydroxy propyl acrylate)
Poly(isobornyl methacrylate)
Poly(iso-butyl methacrylate)
Poly(isocyanato ethyl methacrylate)
Poly(lauryl methacrylate)
Poly(methyl acrylate)
Poly(methyl α-bromoacrylate)
Poly(N,N-dimethylaminoethyl methacrylate)
Poly(2,2,2-Trifluoroethyl methacrylate)
Poly(n-butyl acrylate)
Poly(n-butyl methacrylate)
Poly(neopentyl methacrylate)
Poly(neopentyl acrylate)
Poly(n-hexyl methacrylate)
Poly(n-nonyl acrylate)
Poly(n-nonyl methacrylate)
Poly(n-octyl acrylate)
Poly(n-propyl methacrylate)
Poly(octadecyl methacrylate)
Poly(s-butyl methacrylate)
Poly(t-butyl acrylate)
Poly(t-butyl methacrylate)
Poly(t-butyl α-bromo-acrylate)
Poly(t-butyl α-ethylacrylate)
Poly(t-butyl α-propylacrylate)
Poly(tetrahydrofurfanyl methacrylate)
Poly(2,4-dimethyl-2,4-pentadienoate)
Poly(2-ethyl hexyl acrylate)
Poly(2-hydroxypropyl methacrylate)
Poly(6-(4'-cyanobiphenyl-4-yloxy)hexyl methacrylate)
Polydienes:
Polybutadiene
Polyisoprene
Polyimidazoles:
Poly(N-vinyl imidazole)
Poly(4,5-vinyl imidazole)
Polylactones and Polylactides:
Poly(ϵ-caprolactone)
Poly(Lactide)
Polyolefins:
Polyethylene
Poly(isobutylene)
Polyoxazolines:
Poly(ethyl oxazoline)
Poly(methyl oxazoline)
Polyoxiranes:
Poly(propylene oxide)
Poly(propylene glycol)
Poly(2,6-dimethyl-p-phenylene oxide)
Polypyridines:
Poly(2-vinyl pyridine)
Poly(4-vinyl pyridine)
Poly(2-isopropenyl pyridine)
Poly(2,5-pyridine)
Poly(3,5-pyridine)
Polysiloxanes:
Poly(dimethyl siloxane)
Poly(ethyl methyl siloxane)
Poly(phenyl methyl siloxane)
Poly(diethyl siloxane)
Polystyrenes:
Polystyrene
Poly(α-methyl styrene)
Poly(4-acetoxy styrene)
Poly(3-bromo styrene)
Poly(4-bromo styrene)
Poly(2-chloro styrene)
Poly(3-chloro styrene)
Poly(4-chloro styrene)
Poly(4-dimethylsilyl styrene)
Poly(4-hydroxyl styrene)
Poly(4-methoxy styrene)
Poly(4-methyl styrene)
Poly(4-t-butyl styrene)
Poly(4-(tert-butoxycarbonyl)oxy styrene)
Poly(3-(hexafluoro-2-hydroxypropyl)-styrene
Poly(vinyl benzyl chloride)
Poly(4-vinyl benzoic acid)
Polyvinyl Anthracenes:
Poly(1-vinyl anthracene)
Poly(2-vinyl anthracene)
Poly(9-vinyl anthracene)
Poly(9-vinyl phenanthrene)
Poly(vinyl napthalene)
Poly(acrylonitrile)
Poly(adipic anhydride)
Polyester
Poly(ferrocenyldimethylsilane)
Poly(N-vinyl caprolactam)
Poly(N-vinyl carbazole)
Poly(sulfone ether)
Poly(vinyl acetate)
Poly(carbonate)

Loading Active Agents into TSPs

Three methods are available to encapsulate active agents into TSPs, i.e., (a) one or more active agent is incorporated by flow of the drop through a bulk solution containing the active agent during the particle formation (first self-loading method) (b) one or more active agent is contained in one or more liquid drops initially positioned in sufficiently close proximity to the sedimenting polymer drop to become coalesced or mixed with the latter and for their contents to become entrained (second self-loading method), and (c) TSPs are immersed in an active agent solution after the TSPs are formed (diffusion). In another embodiment, a TSP is loaded using both method (a) or (b) and method (c), which allows for loading of different active agents having the same or different release profiles.

Self-loading is a rapid procedure, in which an active agent is dissolved in the bulk solution, which is miscible with the polymer phase. During formation of the toroidal-spiral structure, an induced flow of the bulk solution past the polymer drop brings the dissolved active agent between forming polymer layers. Because the active agent is not initially mixed with polymer and is not entangled within the polymer matrix, releasing of the active agent may not depend on the pore size of the matrix, which is true for active agent release from a spherical particle. The self-loading method avoids blending an active agent with the polymer before forming the drops (which is the case with spherical particles), and thereby prevents the active agent from being exposed to the high shear fields used in blending processes. Nevertheless, for exceedingly fragile protein molecules, it is possible that the sedimentation flow field involved in manufacturing TSPs could cause denaturation despite the mildness of the present conditions compared to current processes. Exposure of the proteins to crosslinking agents or other crosslinking conditions (such as UV light) might also cause loss of bioactivity in the self-loading method. The light intensity was adjusted to achieve rapid polymer crosslinking, while avoiding protein conformation change. Protein structures were confirmed by circular dichroism (CD).

The second loading method is more mild than the self-loading method, and insures preservation of protein conformations. In this method, after the TSPs are formed, they are immersed into a solution containing one or more active agent. The active agents diffuse into the gaps between the layers of polymer in the TSP. The loaded TSPs are separated from the solution, and formulated to a desired concentration for therapeutic and drug delivery purposes. Loaded TSPs also were rinsed, and placed in a buffer solution for active agent release measurements. In this process, the conditions were very benign, which maintains protein conformation and functionality. For example, the proteins remained in an aqueous solution, were not exposed to high-intensity UV light for extended time periods, and were not subjected to significant temperature fluctuations.

Release of Active Agents from TSPs

Active agents encapsulated in the toroidal-spiral channels release by diffusion out along the spiral path. This process depends upon (1) the geometry of the channels, (2) the diffusivity of the active agents in the liquid inside the channels, and/or (3) viscosity of the liquid in the channels and its diffusivity in the solution surrounding the TSP. Specifically, the viscosity of the channel liquid affects the diffusivity of active agents. There is approximately an inverse relationship between viscosity and diffusivity. Therefore, higher viscosity of the channel liquid yields slower diffusional release of the active agents. There also may be a subtle, compound effect, whereby the high-viscosity channel liquid interdiffuses with the solution surrounding the TSP, and gradually changes its composition to slowly become less viscous. This reduced viscosity then increases the diffusivity of the active agent, thereby increasing the active agent release rate at late stages. The overall release profile therefore can be expected to be more uniform over time with less of a tailing-off at late stages.

Identifying and Monitoring the Release of Active Agent In Vitro

Based on the physical and chemical characteristics of the polymer comprising the TSP, the active agent release mechanism from the polymer matrix is diffusion controlled. Active agent release also can be swell controlled and/or erosion controlled. For a non-biodegradable polymer, active agent release from the TSP results from a concentration gradient by diffusion or enhanced diffusion because of polymer swelling. For a biodegradable polymer matrix, the release rate depends both on diffusion and polymer degradation rates.

An active agent release rate also is related to the identity of active agent, the size of the active agent, and environmental conditions surrounding a TSP. The release rate can be analyzed, for example, by comparing the release profiles of various model proteins from TSPs and from microspheres by using model polymers, such as alginate, PEG, and PLGA.

For prior microspherical particles, release rates for individual active agents were highly variable, depending on the polymer composition, size of the active agents compared to the pore size of the microsphere, the environment, and preparation methods. The molecular weight of the protein and peptide active agents in microspherical particles can vary from about 1 kDa to more than 100 kDa, and release rates from the polymeric particles were highly variable. In contrast, TSPs have well-defined diffusional characteristics associated with the shape of the toroidal-spiral passages inside the particle, with a release rate that is relatively stable, and more readily predictable via theoretical calculation, for various proteins, peptide, and other active agents, and for various polymers.

Release kinetics and diffusion coefficients can be determined using a single-molecule fluorescence correlation spectroscopy (FCS) and a microfluidic system. A microfluidic system integrated with FCS provides a more sensitive determination of diffusion coefficients and release kinetics compared to the bulk experiments. Active agent concentrations in the supernatant and within the TSP both can be determined using the FCS system. The number of the labeled active agent molecules crossing the confocal nanoliter volume can be measured and converted to concentration by using a calibration curve.

A typical release profile of proteins from prior sustained releasing systems is biphasic. An initial rapid initial release (burst effect) is caused by (a) active agent at or near the interface which escapes rapidly into the supernatant solution and (b) active agent close to the larger pores. Later release of the active agent reaches a plateau and rarely reaches 100%. Deviation from the straight line at longer times is associated with non-Fickian diffusion. For present TSPs, compared to prior releasing systems, the diffusion track is well defined and much larger than hydrodynamic diameters of most active agents, including proteins. It is theorized therefore that (a) TSPs can load more active agents due to their large surface to volume ratio; (b) TSPs can provide a sustained release based upon their defined channels; and (c) according to Fick's law, a diffusion coefficient for various proteins can be calculated and compared to the FCS measurements.

FIG. 8 shows the release profiles of BSA up to 25 days after the unloaded TSPs were incubated in a borine serum albumin (BSA) solution for 3 days. In this embodiment, the TSPs were loaded by diffusion. The release rates were measured on single particles. For the same particles, incubation and measurements of release rates were repeated at the same conditions three times. Particles (a) to (d) of FIG. 5 represent four different stages of particle evolution. At later stages of particle evolution, the channels were longer, but narrower. Therefore, BSA was released faster. The control experiment was performed on a semi-spherical particles with same volume of material as the TSPs. For the TSPs at an early stage, it was relatively easier for BSA molecules to diffuse in or out through the TSP channels.

Therefore, the release of BSA was fastest from particle (a) and slowest from particle (d) of FIG. 8. Moreover, because encapsulation was through incubation and diffusion, the amount of BSA encapsulated in particle (a) was the greatest and for particle (d) the least.

The release kinetics of BSA also was measured on the self-loaded TSPs over two weeks, as illustrated in FIG. 9. The measurements were on single particles and were performed on different particles at similar stages. BSA release from the TSPs at an early stage was faster. The sustained release could continue for more than two weeks. Different from incubation loading, the TSPs at later stages encapsulated more proteins by self-loading. The release profile of BSA from particle (1) leveled off after 2 days. Initially, amount of BSA released from particle (3) was least, but the accumulation of release kept increasing, and eventually the amount of BSA release from particle (3) was the highest.

Self-assembled TSPs are a robust system for target delivery and controlled release of therapeutic agents, like proteins and peptides. The release profiles of the loaded therapeutic agent are related to the structure of the TSPs, such as channel width and length, as opposed to molecular size of an active agent or pore size of the polymer matrix. Moreover, essentially all (i.e., greater than 98%) of the protein is released from TSPs rather than trapped in the polymer matrix. Proteins and peptides are encapsulated in the TSP under mild conditions to maintain protein conformation and functionality. Expended TSPs also can be recycled to provide stable and repeatable delivery systems for active agents.

In accordance with an important feature of the present invention, the release rate of an active agent is not dependent on the identity of the active agent. Alternatively stated, from the shape of the TSP, including the number and width of the channels in the TSP, the release rate can be predicted, and is the same for all active agents. As a result, experimentation and trial and error with respect to matching an active agent and a TSP to a release rate is reduced or eliminated.

In addition, although the basic structure of a TSP does not vary, preparation of a TSP can be modified such that a desired release rate is achieved. For example, by increasing the length of time to form the TSP (e.g., a time from a polymer drop contacting the bulk liquid to crosslinking of the resulting TSP), more spirals are formed in the TSP. The formation of additional spirals and channels allows a greater loading of an active agent into the TSP, especially in the self-loading embodiment.

In another process modification, TSPs having wider channels can be prepared by a rapid addition of a plurality of drops, i.e., two or more drops, such as two to about 10 drops, to the bulk solution. The individual drops do not coalesce, but follow one another through the bulk solution, which results in TSPs having wider channels. Wider channels can change the release profile for an active agent and also allows for the loading of various difficult to load active agents, such as large proteins.

EXAMPLES

Materials and Reagents

IRGACURE® 2959 (2-hydroxy-1-[4-(2-hydroxyethoxyl) phenyl]-2-methyl-1-propanone) (1-2959) is available from Ciba Specialty Chemicals (Basel, Switzerland). Poly(ethylene glycol) diacrylate (PEG-DA) (Mw 700), glycerol, and bovine serum albumin (BSA) were purchased from Sigma-Aldrich (St. Louis, Mo.). Micro BCA protein assay kit was purchased from Thermo Fisher Scientific (Rockford, Ill.). All chemicals were purchased at standard grades and used as received.

Toroidal-Spiral (TSP) Preparation

The photoinitiator (1-2959) was dissolved in ethanol at 25 wt %. PEG-DA (700) and the photoinitiator solution were mixed in a 4:1 volume ratio. Glycerol was mixed with ethanol and used as the bulk phase solution. Polymer drops (8.5 μL) were made by using a syringe pump (Harvard Apparatus, PHD 2000 programmable, Holliston, Mass.) with a flow rate of 85 μL/min. The drops fell from a flat tipped needle (Hamilton Company, 22G PS3, Reno, Nev.) held at a height above the bulk solution. Once the polymer solution was pumped from the syringe, the solution was accumulated at the tip of the needle until the surface tension could not balance gravity. Therefore, the initial velocity of the polymer drop can be neglected. When the polymer drop entered interface of bulk solution and air, the potential energy of the drop was transformed to kinetic energy. As the drop descended through solution, the drop rolled up into a toroidal spiral and was instantly crosslinked photochemically at different stages of layer formation using UV light (Dymax, Bluewave 75, Torrington, Conn.).

Viscosity Measurements

In the self-assembling process to produce TSPs, a viscosity ratio of the polymer (drop) phase to bulk phase close to unity is preferred, but not required. The viscosity of polymer solutions at different concentrations of glycerol was measured using a rheometer (Anton Paar, Physica MCR 301, Osterreich, Austria). Concentrations of glycerol in ethanol ranged from 60 wt % to 65 wt % were made, and viscosities were plotted against shear stress of the solution. The measurements indicated that for PEG-DA 700, the polymer solution is a Newtonian fluid and its viscosity was most similar to the viscosity of 63 wt % glycerol mixed with ethanol.

For protein self-loading during the TSP formation, BSA was dissolved in the bulk solution. A 10 mg/mL, presence of BSA in the bulk solution had no effect on the viscosity of the solution.

High Speed Camera Images

TSP formation of layers was observed under high speed camera (Vision Research, Phantom v12.1, Wayne, N.J. and Allied Vision Technology, Prosilica GX 1050, Stadtroda, Germany) set to 110 frames per second. A microscope lens (Infinity Photo-Optical Company, K2/SC, Boulder, Colo. and Computar, MLH-10X, Commack, N.Y.) was attached to the camera for a higher magnification. The lens was placed about six to twelve inches away from a glass vessel containing bulk phase solution. The cross section of the glass vessel was rectangular (1.5 inch×2 inch) to avoid boundary and curvature effects. Exposure was set to 1000 microseconds. The camera was used to study the TSP evolution and ensure the morphology of the TSPs while a TSP was crosslinked under the UV light.

SEM Images

The solid TSPs were dehydrated by placing the particles in a solution of ethanol in deionized water (DI water, 1:1 weight ratio) for twenty minutes, then increasing the concentration of ethanol by 10 wt % every twenty minutes. The TSPs then were placed in pure ethanol for another 20 minutes. The TSPs then were cut using a very thin blade (Ted Pella Inc., Feather Double-Edge Blade, Redding, Calif.). The dissected particles were placed into a desiccator under vacuum for at least ten minutes to remove moisture. Once dried, particles were placed on carbon planchet stubs and coated with 5 nm gold using sputter coater. SEM (Hitachi Scientific Instruments, S-3000N, Tokyo, Japan) images were taken of the coated particles.

Protein Encapsulation

Two ways to load BSA on TSPs were used, self loading and incubation. In the process of protein self-loading, BSA was added into the bulk phase. The convective process automatically loaded proteins inside the TSPs during formation. The composition of the bulk phase was 61 wt % glycerol, 35 wt % ethanol, 3.6 wt % DI water, and 0.4 wt % BSA, which was chosen to achieve a viscosity ratio of the polymer (drop) phase to bulk phase close to unity. To prepare the bulk solution, BSA was dissolved in DI water first, then glycerol was added to the solution. Finally, ethanol was added to the well-mixed solution. The conformation of BSA was confirmed by circular dichroism (CD) measurements. BSA (0.4 wt %) in the bulk solution was a preferred concentration to produce TSPs with stable and repeatable structures and obtain highest protein concentration.

In the process of loading protein incubation by polymer drops were crosslinked in the bulk solution of 63 wt % glycerol and 37 wt % ethanol. The solid TSPs then were placed in a solution of 55 mg/mL BSA dissolved in DI-water. Each particle was incubated for 72 hours.

Protein Release Experiments

Before measuring BSA release from the TSPs, the TSPs were rinsed, the placed in 500 uL phosphate buffered saline (PBS). The buffer was completely replaced at specific time intervals with fresh PBS. The amount of protein released was measured with Micro BCA kit.

In summary, the present invention provides the following nonlimiting advantages: (a) TSPs of controlled size are formed by matching gravitational sedimentation, viscous force, and diffusion of a polymer drop falling or rising within a second bulk liquid phase in which the polymer drop is soluble. By matching the sedimentation force, viscosity ratio, polymer concentration, ionic concentration, and the size of the drop, optimized conditions can be attained; (b) non-Newtonian polymer drops form toroidal spiral structures similar to Newtonian drops; (c) the sedimenting polymer drops take up active agent during formation of the TSP; (d) flow parameters and relevant timescales are selected such that diffusion does not substantially modify the purely convective phenomena in the formation of a TSP; (e) the polymeric drops are solidified by crosslinking (i) in an appropriate chemical crosslinker (e.g., calcium chloride) or (ii) with exposure to UV light; (f) active agents encapsulated in the toroidal spiral particles are bioactive and released by diffusion or degradation; (g) TSPs are biocompatible; (h) TSP suspensions can be delivered by injunction, by implantation after surgery, transdermal drug delivery, and aerosol drug delivery; (j) the size and density of the TSPs are suitable for deep-lung aerosol deposition; and (h) the TSPs release active agents in the lungs.

1. S. Koutsopoulos et al., *Proceedings of the National Academy of Sciences of the United States of America,* 2009. 106(12): p. 4623-4628.
2. D. Chen et al., *Proceedings of the National Academy of Sciences of the United States of America,* 2008. 105(44): p. 16843-16848.
3. A. Afuwape et al., *Histology and Histopathology,* 2002. 17(3): p. 961-972.
4. M. J. Post et al., *Cardiovascular Research,* 2001. 49(3): p. 522-531.
5. S. Yla-Herttuala et al., *Cardiovascular gene therapy. Lancet,* 2000. 355(9199): p. 213-222.
6. B. S. Lewis et al., *Cardiovascular Research,* 1997. 35(3): p. 490-497.
7. O. G. Kolterman et al., *American Journal of Health-System Pharmacy,* 2005. 62(2): p. 173-181.
8. S. D. Putney et al., *Nature Biotechnology,* 1998. 16(2): p. 153-157.
9. R. J. Laham et al., *Circulation,* 1999. 100(18): p. 1865-1871.
10. C. M. Dobson, *Principles of protein folding, misfolding and aggregation.* Seminars in Cell & Developmental Biology, 2004. 15(1): p. 3-16.
11. C. M. Dobson, *Methods,* 2004. 34(1): p. 4-14.
12. C. M. Dobson, *Nature,* 2003. 426(6968): p. 884-890.
13. M. Stefani et al., *Journal of Molecular Medicine-Jmm,* 2003. 81(11): p. 678-699.
14. R. Krishnamurthy et al., *Current Pharmaceutical Biotechnology,* 2002. 3(4): p. 361-371.
15. M. Fedakar-Senyucel et al., *Journal of Pediatric Surgery,* 2008. 43(2): p. 290-295.
16. K. A. Dill, Biochemistry, 1990. 29(31): p. 7133-7155.
17. S. L. Tao et al., *Advanced Drug Delivery Reviews,* 2003. 55(3): p. 315-328.
18. M. Gandhi et al., *Molecular Pharmaceutics,* 2009. 6(2): p. 641-647.
19. H. Tamber et al., *Advanced Drug Delivery Reviews,* 2005. 57(3): p. 357-376.
20. H. J. Chung et al., *Pharmaceutical Research,* 2006. 23(8): p. 1835-1841.
21. Y. Itoh et al., *Biomacromolecules,* 2008. 9(8): p. 2202-2206.
22. F. M. Veronese et al., *Advanced Drug Delivery Reviews,* 2002. 54(4): p. 453-456.
23. J. Markussen et al., *Diabetologia,* 1996. 39(3): p. 281-288.
24. T. R. Hoare et al., *Polymer,* 2008. 49(8): p. 1993-2007.
25. M. J. B. Wissink et al., *Journal of Controlled Release,* 2000. 64(1-3): p. 103-114.
26. S. Schulze et al., *Journal of Controlled Release,* 2009. 134(3): p. 177-185.
27. V. F. M. Segers et al., *Drug Discovery Today,* 2007. 12: p. 561-568.
28. H. Lee et al., *Pharmaceutical Research,* 2002. 19(6): p. 845-851.
29. G. Machu et al., *Journal of Fluid Mechanics,* 2001. 447: p, 299-336.
30. L. C. Nitsche et al., *Computers and Chemical Engineering,* 2004. 28: p. 187301879.
31. J. Happel et al., *Low Reynolds Number Hydrodynamics: With Special Applications to Particulate Media.* 1983: *Kluwer.*
32. S. Kim et al., *Microhydrodynamics: Principles and Selected Applications.* 2005 (Originally 1991): Dover.
33. A. M. Blandino et al., *Journal of Bioscience and Bioengineering,* 1999. 88(6): p. 686-689.

34. Y. Murata et al., *Journal of Controlled Release,* 1993. 23(1): p. 21-26.
35. N. P. Desai et al., *Journal of Biomedical Materials Research,* 1991. 25(7): p. 829-843.
36. M. B. Mellott et al., *Biomaterials,* 2001. 22(9): p. 929-941.
37. J. L. Hillwest et al., *Proceedings of the National Academy of Sciences of the United States of America,* 1994. 91(13): p. 5967-5971.
38. A. S. Sawhney et al., *Journal of Biomedical Materials Research,* 1994. 28(7): p. 831-838.

Obviously, many modifications and variations of the invention as hereinbefore set forth can be made without departing from the spirit and scope thereof and, therefore, only such limitations should be imposed as are indicated by the appended claims.

The invention claimed is:

1. A particle delivery system comprising polymeric toroidal-spiral particles, the polymeric toroidal-spiral particles comprising a polymeric matrix, a first active agent, and a second active agent, wherein the first active agent resides within the polymeric matrix and the second active agent resides on surfaces of the toroidal-spiral particles and within open channels of the toroidal-spiral particles, and wherein the second active agent comprises one or more of a protein and a peptide.

2. The particle delivery system of claim 1 wherein the first active agent comprises a small molecule drug.

3. The particle delivery system of claim 2 wherein the small molecule drug is selected from the group consisting of doxorubicin, doxorubicin-galactosamine, camptothecin, paclitaxel, a palatinate, ethylenimines, imidazotetrazines, nitrogen mustard analogs, nitrosoureas, platinum-containing compounds, antimetabolites, purine analogs, pyrimidine analogs, urea derivatives, antracyclines, actinomycins, camptothecin derivatives, neuromuscular paralytic agents, CNS stimulants, dopaminergic reagents, monoamine oxidase inhibitors, COMT inhibitors, alkyl sulphonates, epipodophyllotoxins, taxanes, vinca alkaloids, antiandrogens, antiestrogens, nonsteroidal aromatase inhibitors, protein kinase inhibitor antineoplastics, azaspirodecanedione derivatives, anxiolytics, monoamine reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonists, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, lidocaine, articaine hydrochloride, bupivacaine hydrochloride, antipyretics, hynotics, sedatives, cyclopyrrolones, pyrazolopyrimidines, nonsteroidal anti-inflammatory drugs, opioids, para-aminophenol derivatives, alcohol dehydrogenase inhibitor, and heparin antagonists.

4. The particle delivery system of claim 1 wherein the particles have a particle size of about 10 μm to about 10 mm.

5. The particle delivery system of claim 1 wherein the open channels of the toroidal-spiral particles are about 1 μm to about 10 μm in width.

6. The particle delivery system of claim 1 wherein the polymeric matrix comprises a polyethylene glycol, alginic acid, a poly(ethylene glycol) diacrylate polymer, poly(D,L-lactide-co-glycolide), a polyphosphazene, a polysaccharide, polysialic acid, pullulane, chitosan, hyaluronic acid, chondroitin sulfate, dermatan sulfate, starch, dextran, carboxymethyl-dextran, polyalkylene oxide, copolymers of polyalkylene oxides, polyoxamer, polyalkylene glycol, polypropylene glycol, polyoxazoline, polyacryloylmorpholine, polyvinyl alcohol, polycarboxylate, polyvinylpyrrolidone, polyphosphazene, polyethylene-co-maleic acid anhydride, polystyrene-co-maleic acid anhydride, poly(l-hydroxymethylethylene hydroxymethylformal), 2-methacryloyloxy-2'-ethyltrimethylammonium phosphate, or mixtures thereof.

7. The particle delivery system of claim 1 wherein the polymer matrix is crosslinked.

8. The particle delivery system of claim 1 wherein an open channel volume of the toroidal-spiral particles is about 5% to about 60%, in relation to the total volume of the toroidal-spiral particles.

9. The particle delivery system of claim 1 wherein the one or more of a protein and a peptide is selected from the group consisting of transforming growth factor-α bovine serum albumin, insulin, epidermal growth factor, basic fibroblast growth factor, transforming growth factor-β, bone morphogenetic protein, vascular endothelial growth factor, immunoglobulin G, erythropoietin, Factor H, Factor VIII, von Willebrand Factor, Factor Vila, Factor IX, interferon α2a, interferon α2b, growth hormone receptor agonist, granulocyte colony-stimulating factor, anti-vascular endothelial growth factor aptamer, anti-tumor necrosis factor Fab, and diFab antibody.

10. The particle delivery system of claim 1 wherein the first active agent and the second active agent are identical.

11. The particle delivery system of claim 1 wherein the first active agent and the second active agent are different.

12. The particle delivery system of claim 1 wherein the first active agent comprises one or more of a protein and a peptide.

* * * * *